United States Patent
Ho et al.

(10) Patent No.: US 10,739,336 B2
(45) Date of Patent: Aug. 11, 2020

(54) MAGNETIC PLATFORM FOR DIRECT AND MULTIPLEX IMMUNE-BASED DETECTION OF TRACE AMOUNT OF PROTEIN BIOMARKERS

(71) Applicant: Hong Kong Baptist University, Hong Kong (HK)

(72) Inventors: See Lok Ho, Hong Kong (HK); Hei Nga Chan, Hong Kong (HK); Di Xu, Hong Kong (HK); Hung Wing Li, Hong Kong (HK); Ricky Man Shing Wong, Hong Kong (HK)

(73) Assignee: Hong Kong Baptist University, Hong Kong (CN)

( * ) Notice: Subject to any disclaimer, the term of this patent is extended or adjusted under 35 U.S.C. 154(b) by 192 days.

(21) Appl. No.: 15/276,811

(22) Filed: Sep. 27, 2016

(65) Prior Publication Data

US 2017/0097340 A1    Apr. 6, 2017

Related U.S. Application Data

(60) Provisional application No. 62/236,123, filed on Oct. 1, 2015.

(51) Int. Cl.

| | | |
|---|---|---|
| G01N 33/53 | (2006.01) | |
| G01N 33/543 | (2006.01) | |
| G01N 33/58 | (2006.01) | |
| G01N 33/574 | (2006.01) | |

(52) U.S. Cl.
CPC .  *G01N 33/54326* (2013.01); *G01N 33/54373* (2013.01); *G01N 33/57484* (2013.01); *G01N 33/582* (2013.01); *G01N 2800/2821* (2013.01)

(58) Field of Classification Search
None
See application file for complete search history.

(56) References Cited

U.S. PATENT DOCUMENTS

| | | | | |
|---|---|---|---|---|
| 4,578,349 | A * | 3/1986 | Schaffel | G01N 33/57473 435/7.23 |
| 2007/0054407 | A1 * | 3/2007 | Chen | B82Y 15/00 436/86 |
| 2014/0336068 | A1 * | 11/2014 | Hodges | C12Q 1/6804 506/9 |
| 2015/0024415 | A1 * | 1/2015 | Lu | C12Q 1/42 435/7.72 |

OTHER PUBLICATIONS

Chozinski et al., Twinkle, twinkle little star: Photoswitchable fluorophores for super-resolution imaging, FEBS Letters, 588, Jul. 2014 , pp. 3603-3612. (Year: 2014).*

* cited by examiner

*Primary Examiner* — Gary Counts
(74) *Attorney, Agent, or Firm* — Spruson & Ferguson (Hong Kong) Limited

(57) ABSTRACT

The present invention discloses a magnetic platform for direct and multiplex immune-based detection of trace amount of protein biomarkers for cancers, neurodegenerative disease such as Alzheimer's disease

7 Claims, 20 Drawing Sheets

MAGNETIC PLATFORM FOR DIRECT AND MULTIPLEX IMMUNE-BASED DETECTION OF TRACE AMOUNT OF PROTEIN BIOMARKERS

CROSS-REFERENCE TO RELATED APPLICATIONS

This application claims the benefit of U.S. Provisional Patent Application Ser. No. 62/236,123 filed Oct. 1, 2015; the disclosures of which are incorporated herein by reference in their entirety.

FIELD OF THE INVENTION

The present invention relates to a method with magnetic platform for direct and multiplex immune-based detection of trace amount of protein biomarkers for diseases, such as cancers and neurodegenerative disease like Alzheimer's disease. More particularly, it relates to an useful tool or technique for early disease diagnostics.

BACKGROUND OF THE INVENTION

Detection of biomarkers has been considered as an useful tool for diagnosis, especially for early disease diagnosis. Many sandwich immunoassays, such as electrochemiluminescence immunoassay, enzyme immunoassay, and immunoassay with fluorescence labels, such as quantum dots and commercially available fluorophores tagged antibody, have been developed for the detection of disease related to protein biomarkers.

Nonetheless, to quantify trace amount of protein biomarkers in complex sample matrix, those immunoassays often require a relatively large amount of raw sample (tens to hundreds microliter), multiple purification, pre-treatment and enrichment steps. The tedious pretreatment steps often cause sample loss and hence hindered the accuracy and throughput of the detection assay. Hence, a direct, simple, specific, sensitive and accurate detection is highly in demand. It is the objective of the present invention to provide a direct, simple, specific, sensitive and accurate detection solution.

SUMMARY OF THE INVENTION

In accordance with a first aspect of the present invention, there is provided a method with magnetic platform for direct and multiplex immune-based detection of trace amount of protein biomarkers for diseases, such as cancers and Alzheimer's disease. Benefit from the unique signal enhancement property of the switch-on fluorophores and the high signal-to-noise ratio property of the total internal reflection fluorescence microscopy of the present invention, the present invention has an impressive detection limit down to the femto-molar regime without sample amplification and pretreatment. Detection in pico-molar regime can be achieved by conventional commercial spectrofluorimeter, or other forms of fluorescence spectroscopy. The present invention can also efficiently discriminate the target proteins of virtually any kind of protein biomarkers from complex matrix proteins by varying the antibodies used in the present invention and quantify trace amount of target protein in biological samples, such as cerebrospinal fluid (CSF) and serum sample. The present invention serves as an useful tool or technique for early disease diagnostics.

In accordance with a second aspect of the present invention, there is provided a method and apparatus for detection of trace amount of target biomarkers in a biological medium. The method comprises conjugating at least one capturing antibody onto the surface of at least one silicon-coated magnetic nanoparticle to form at least one detection probe; introducing said detection probe and at least one detection antibody into said biological medium to capture at least one target antigen wherein said target antigen is said target biomarkers or an antigen that is associated with said target biomarkers; capturing said target antigen on the surface of said silicon-coated magnetic nanoparticle via the capturing antibody and the detection antibody to form at least one sandwich magnetic immuno-composite; labelling said magnetic immuno-composite with at least one switched-on fluorophore to form at least one fluorescent magnetic immuno-composite; separating said fluorescent magnetic immuno-composite from the biological medium using at least one magnet, and detecting said separated fluorescent magnetic immuno-composite using at least one fluorescent detection means.

In a first embodiment of the second aspect of the present invention, there is provided a method and apparatus for detection of trace amount of target biomarkers in a biological medium wherein said target biomarkers comprises protein biomarkers.

In a second embodiment of the second aspect of the present invention, there is provided a method and apparatus for detection of trace amount of target biomarkers in a biological medium wherein said biological medium is bodily fluids. The bodily fluids include sera, urine, saliva and cerebrospinal fluid.

In a third embodiment of the second aspect of the present invention, there is provided a method and apparatus for detection of trace amount of target biomarkers in a biological medium wherein said at least one capturing antibody comprising cancer related antibodies, nucleic-acid probes (DNA and/or RNA), aptamers or a combination thereof.

In a fourth embodiment of the second aspect of the present invention, there is provided a method and apparatus for detection of trace amount of target biomarkers in a biological medium wherein said at least one silicon-coated magnetic nanoparticle comprising silicon-coated iron oxide nanoparticles.

In a fifth embodiment of the second aspect of the present invention, there is provided a method and apparatus for detection of trace amount of target biomarkers in a biological medium wherein said at least one detection antibody comprising cancer related antibodies, nucleic-acid probes (DNA and/or RNA), aptamers or a combination thereof.

In a sixth embodiment of the second aspect of the present invention, there is provided a method and apparatus for detection of trace amount of target biomarkers in a biological medium wherein said at least one target antigen comprising cancer-associated antigens and Alzheimer's Diseases protein biomarkers.

In a seventh embodiment of the second aspect of the present invention, there is provided a method and apparatus for detection of trace amount of target biomarkers in a biological medium wherein said at least one switched-on fluorophore comprising SPAce, VLAce, SLAce, SIM, SIOH or a combination thereof.

In an eighth embodiment of the second aspect of the present invention, there is provided a method and apparatus for detection of trace amount of target biomarkers in a biological medium wherein said at least one magnet comprising one or more external magnets.

In a ninth embodiment of the second aspect of the present invention, there is provided a method and apparatus for detection of trace amount of target biomarkers in a biological medium wherein said at least one fluorescent detection apparatus comprising fluorescent microscopy, fluorescence spectroscopy or a combination thereof.

Those skilled in the art will appreciate that the invention described herein is susceptible to variations and modifications other than those specifically described.

The invention includes all such variation and modifications. The invention also includes all of the steps and features referred to or indicated in the specification, individually or collectively, and any and all combinations or any two or more of the steps or features.

Other aspects and advantages of the invention will be apparent to those skilled in the art from a review of the ensuing description.

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE INVENTION

The present invention is not to be limited in scope by any of the specific embodiments described herein. The following embodiments are presented for exemplification only.

Figure 1:
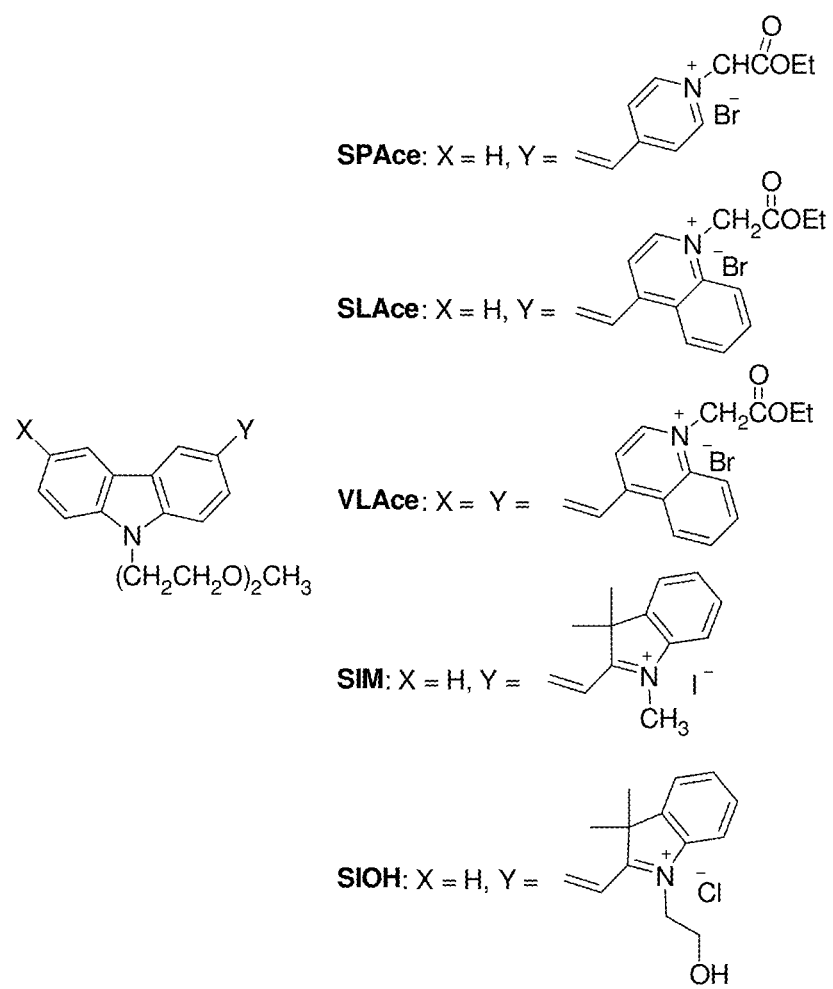
FIG. 1 shows the chemical structures of the five switch-on fluorophores of the present invention.

Without wishing to be bound by theory, the inventors have developed an assay with magnetic platform for direct and multiplex immuno-based detection of trace amount of protein biomarkers for cancers and Alzheimer's disease. Benefit from the unique signal enhancement property of the switch-on fluorophores and the high signal-to-noise ratio property of the total internal reflection fluorescence microscopy of the present application, the present method has an impressive detection limit down to the femto-molar regime without sample amplification and pretreatment. Detection in pico-molar regime can also be achieved by conventional commercial spectrofluorimeter. The present invention is also highly selective and is able to efficiently discriminate the target proteins, virtually any kind of protein biomarkers, from complex matrix proteins and quantify the trace amount of target protein in biological samples, such as cerebrospinal fluid (CSF) and serum samples. The present invention serves as a useful tool for early disease diagnostics. To enhance the sensitivity of the detection assay, in this invention, five switch-on fluorophores which are excited at 488-nm but emit at distinguishable peak wavelengths (Table 1) are provided and used for such multiplex detection. The chemical structures of these fluorophores are depicted in FIG. 1.

TABLE 1

Summary of the physical properties of the switch-on cyanine fluorophores.

| | $\lambda^{abs}_{max}$[a] (nm) | $\lambda^{em}_{max}$[a] (nm) | $\Phi_{PL}$[b] | $\lambda^{em}_{max}$[c] (nm) |
|---|---|---|---|---|
| SPAce | 429 | 588 | 0.015 | 572 |
| SLAce | 478 | 681 | 0.0034 | 654 |
| VLAce | 524 | 723 | 0.0007 | 754 |
| SIM | 475 | 597 | 0.18 | — |
| SIOH | 481 | 598 | 0.11 | — |

[a]measured in phosphate buffer
[b]using Rhodamine 6G ($\Phi_{488}$ = 0.95) as standard
[c]Emission maximum upon binding to the PSA magnetic nanocomposites.

Figure 2A:
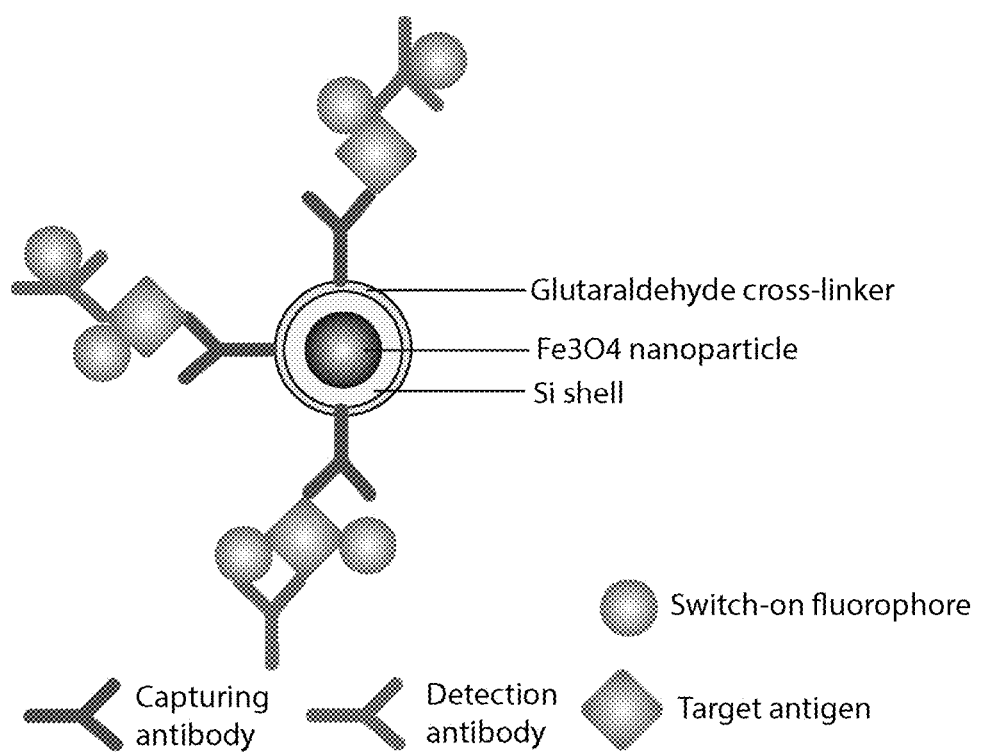
FIG. 2a shows the schematic illustration of the switch-on fluorophore labeled sandwiched magnetic immunocomposite. The capture antibody is conjugated onto the surface of silicon-coated iron oxide nanoparticles. The target protein biomarker molecules are first selectively captured by the capturing antibody and detection antibody and then labeled with the switch-on fluorophores.
Figure 2B:
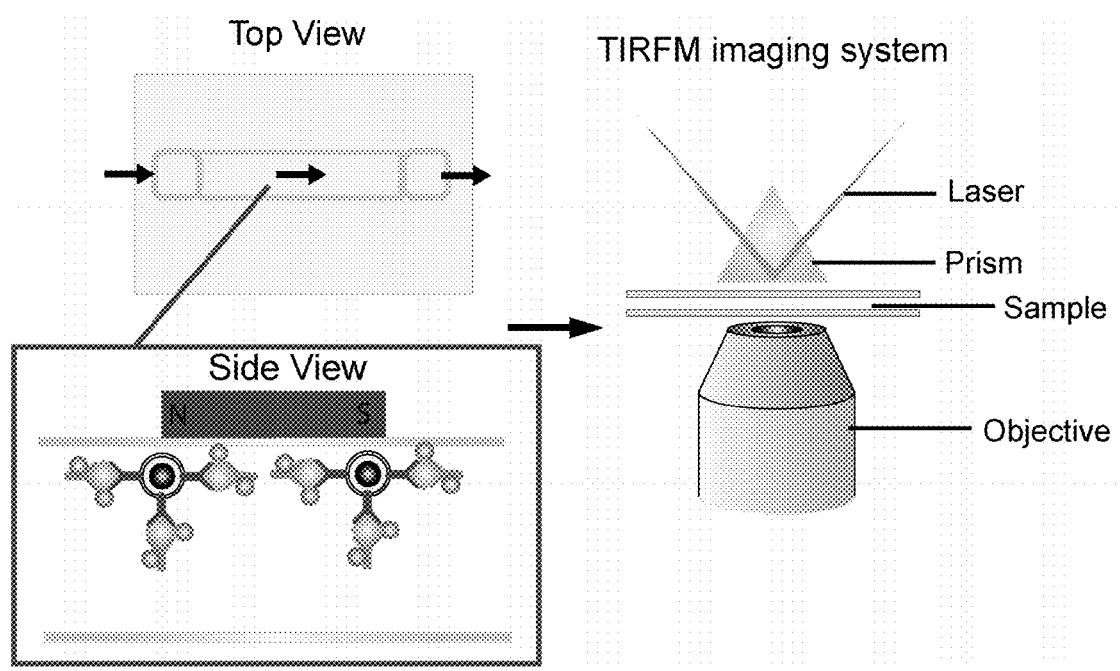
FIG. 2b shows schematic illustration of direct quantification of fluorescent immunocomposite with TIRFM. Single nanoparticle is imaged and the fluorescence intensity from each individual are measured and analyzed.

The overall detection scheme of the present invention is illustrated in FIGS. 2a and 2b. The capturing antibody (Ab1) is first immobilized onto the surface of the silicon-coated iron oxide nanoparticles (IONP)—this is one embodiment of a silicon-coated magnetic nanoparticle, and acted as a detection probe. In one embodiment, the present invention includes an array of IONP with the capturing antibody immobilized on the surface. Ab1 is specific to the target protein or antigen. Then the detection probe and the detection antibody (Ab2) are added to the sample to capture the target antigen and formed a sandwich magnetic immunocomposite on the surface of the IONP. Ab2 is an antibody having specificity to the target biomarker, protein and antigen. Types of Ab1 and Ab2 may be varied in the present invention to detect different target antigens, proteins and biomarkers. The sandwich magnetic immuno-composites (MICs) are then labeled by switch-on fluorophore to form fluorescent sandwich magnetic immuno-composite. The switch-on fluorophore binds to Ab1, Ab2 and/or the target antigen, proteins or biomarkers via electrostatic interaction and/or hydrophobic interaction. The fluorescent MICs are then injected into a home-built flow cell; the flow cell is made by joining two glass-coverslips with double-sided adhesive tape, the dimension of the channel is but not limited to approximately 3×20 mm. After the injection, the MICs are then separated from the bulk solution and immobilized on the top coverslip by an external magnetic field. Then the fluorescent images of the MICs are visualized under the Total Internal Reflection Fluorescence Microscope-Electron Multiplying Charge Coupled Device (TIRFM-EMCCD) imaging system with a 488 nm cyan laser may be used as the excitation source for quantitative analysis. The evanescent field generated by the total internal reflection is very shallow (~300 nm thick), only sample within the evanescent field is excited by the laser (in this case the samples within the field are the MICs immobilized on the top of coverslip), while the rest in the bulk solution remains silent. Single MICs are imaged by an EMCCD. The intensity of the MICs collected by the EMCCD is proportional to the amount of the target protein captured. The application of TIRFM improves the signal-to-noise of the images. The difference in fluorescence intensity with and without the target antigens is compared to determine the concentration of the target antigen. By incorporating all the advantages of the switch-on fluorophores, magnetic nanoparticles and the TIRFM imaging system, the present invention is highly sensitive, specific, and capable of performing multiplex detection of the trace amount of biomarkers in complex sample matrix in a high-throughput manner.

To demonstrate the present invention, three different cancer-associated antigens, alpha-fetoprotein (AFP), carcinoembryonic antigen (CEA), and prostate specific antigen (PSA) are chosen as the model target protein biomarkers. The present invention is able to detect other biomarkers and antigens. The cancer-associated antigens described herein are presented for demonstration only. The present invention is not limited to the examples described herein. One skilled in the art will appreciate that the present invention may be varied and practiced without departing the scope of the invention. AFP is a biomarker that is well known to be associated with hepatocellular carcinoma and other malignancies. Abnormal concentration of CEA and PSA in serum is a sign of colon cancer and prostate cancer, respectively. The present invention is capable of detecting and quantifying the amount of antigens in serum sample and the result is further validated by conventional enzyme-linked immunosorbent assay (ELISA).

Figure 3:
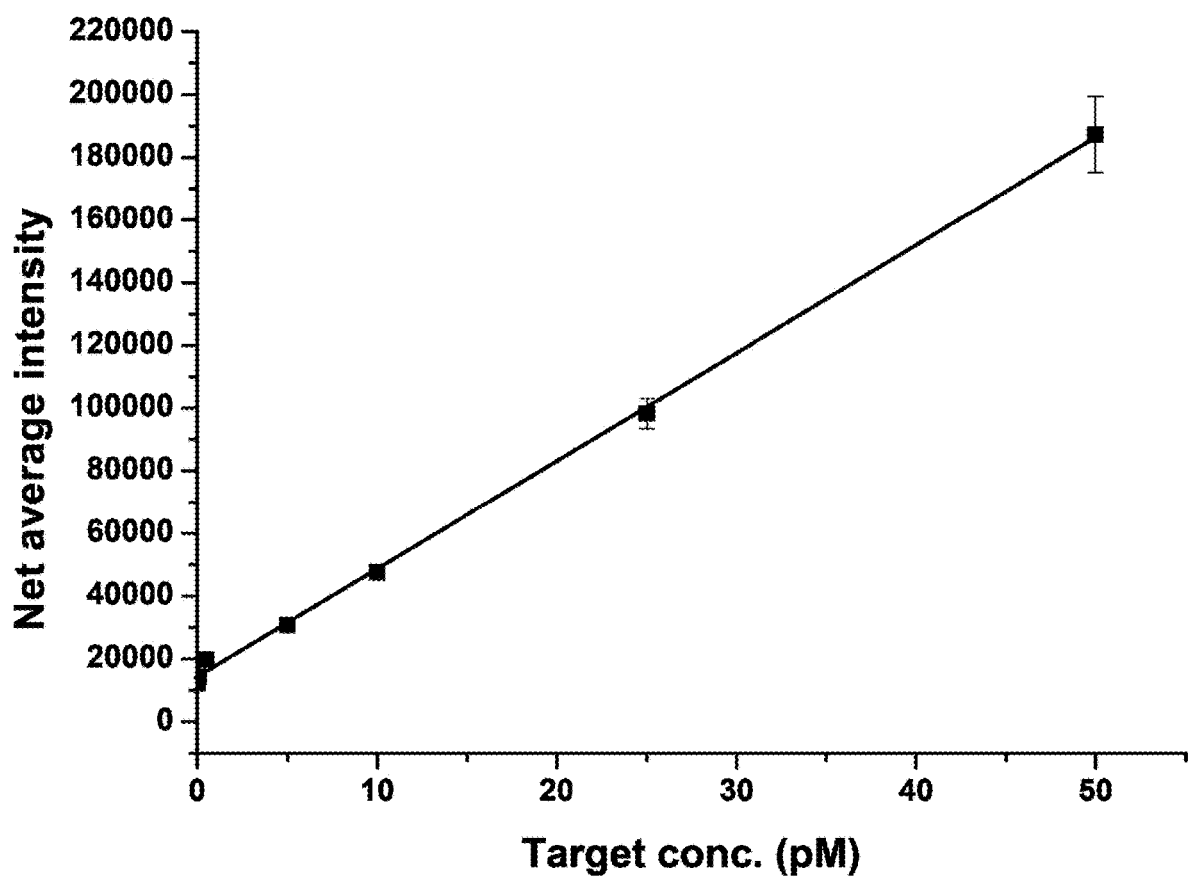
FIG. 3 shows the calibration plot for the quantification of PSA, different concentrations of PSA are incubated with the capturing and the detection antibody.

To demonstrate the performance of the present invention, a calibration plot of the average net intensity as a function of the concentration of the target PSA is constructed under the method as mentioned above. In the example, PSA of concentration ranged from 0 to 20 pM, is incubated with 10 mg/mL Ab1-MNPs for PSA and 100 pM Ab2 for PSA, at 37° C. The resultant MICs are then labeled with 100 μM SLAce, injected into the flow cell and adsorbed onto the surface of the flow cell through an external magnetic force. By measuring the fluorescence intensity of 50 individual MICs as a function of target PSA concentration, the calibration curve (FIG. 3) is constructed with a good linear correlation coefficient, $R^2$=0.996. A limit of detection of 200 fM (6.5 pg/mL) (LOD=blank+3×standard error of mean of blank) and a limit of quantification of 2 pM (0.66 ng/mL) are achieved. As the universal cut-off value of PSA for biopsy is set at 4 ng/mL, the present invention is capable of quantifying PSA in the range of femtomolars in serum samples for clinical applications.

Figure 4:
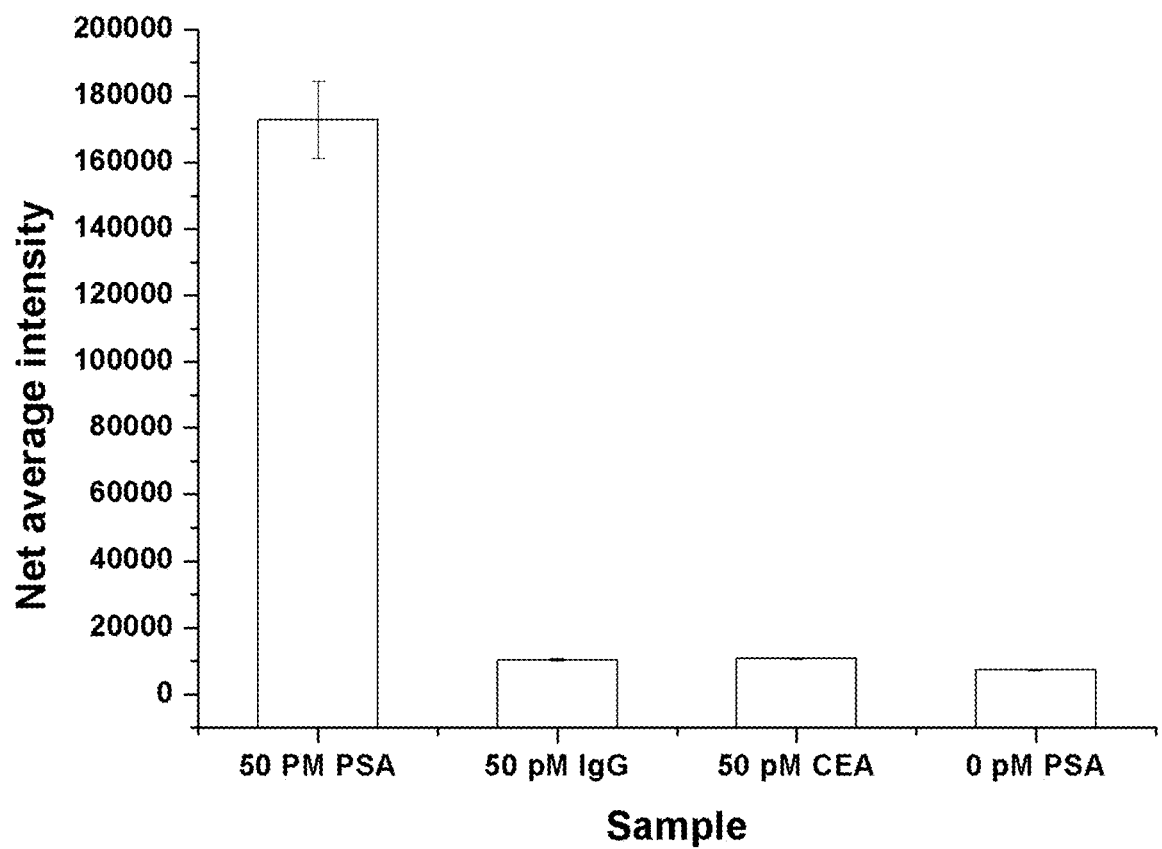
FIG. 4 shows the study of the selectivity of capturing antibody (Ab1) conjugated nanoparticles and detection antibody (Ab2) for PSA. The probe is capable of differentiating the target from other protein molecules. It indicates that the Ab1 conjugated nanoparticles and the Ab2 have a high binding affinity towards the target biomarker molecules and capable of discriminating target antigen from the others.

To demonstrate the selectivity of the present invention, three different human antigens samples (CEA, PSA and IgG) of a final concentration of 50 pM are incubated with 10 mg/mL capturing antibody conjugated nanoparticles for PSA (Ab1) and 100 pM detection antibody for PSA (Ab2) and labeled with 100 μM SLAce. IgG is the major component and the most abundant antibody isotype in human serum. The fluorescent images of the sandwich fluorescence MICs are captured under the TIRFM imaging system. As illustrated in FIG. 4, the false hit rate in samples containing CEA and IgG is less than 10%. It indicates that the Ab1 conjugated nanoparticles and the Ab2 have a high binding affinity towards the target and capable of discriminating target antigens from the others.

Figure 5:
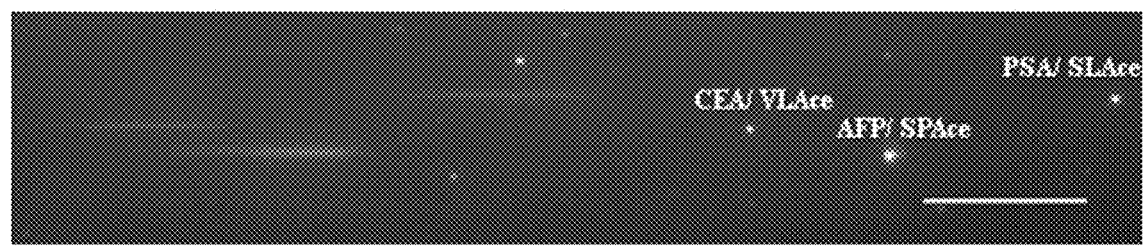
FIG. 5 shows the multiplex detection of the cancer associated antigen: zero and first order image of the immunocomposites labeled with SPAce, SLAce and VLAce, respectively (top), and emission spectra of magnetic immunocomposites (bottom). The emission profiles of the three switch-on fluorophores are readily distinguishable from each other.
Figure 5:
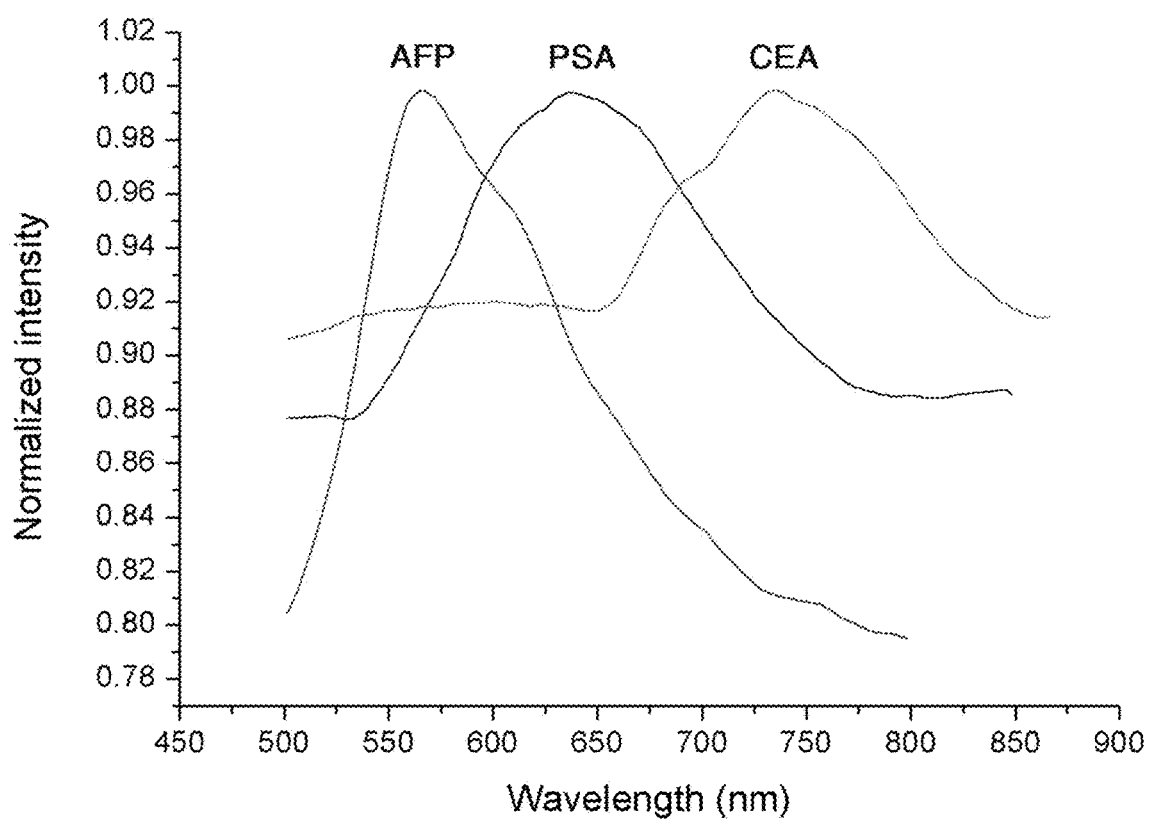
Figure 6:
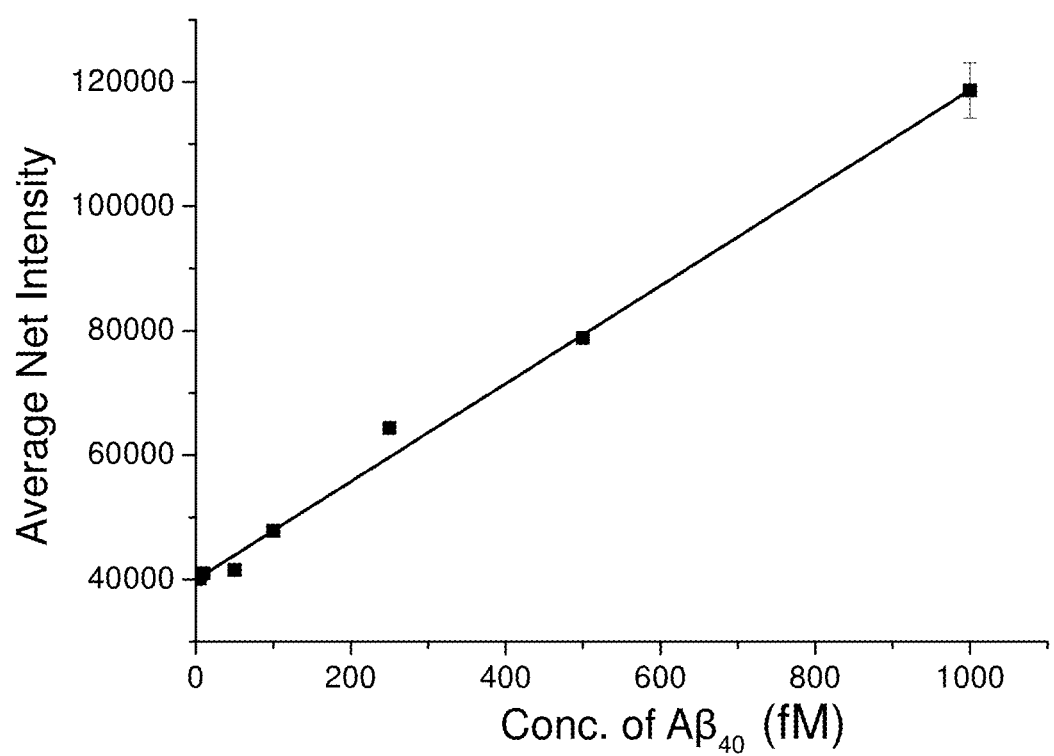
FIG. 6 shows the calibration plot for the quantification of $A\beta_{40}$ using SLAce, different concentrations of $A\beta_{40}$ are incubated with the nano-magnetic probes and the detection antibody. Error bars, standard error of mean n=3. Limit of detection=50 fM.
Figure 7:
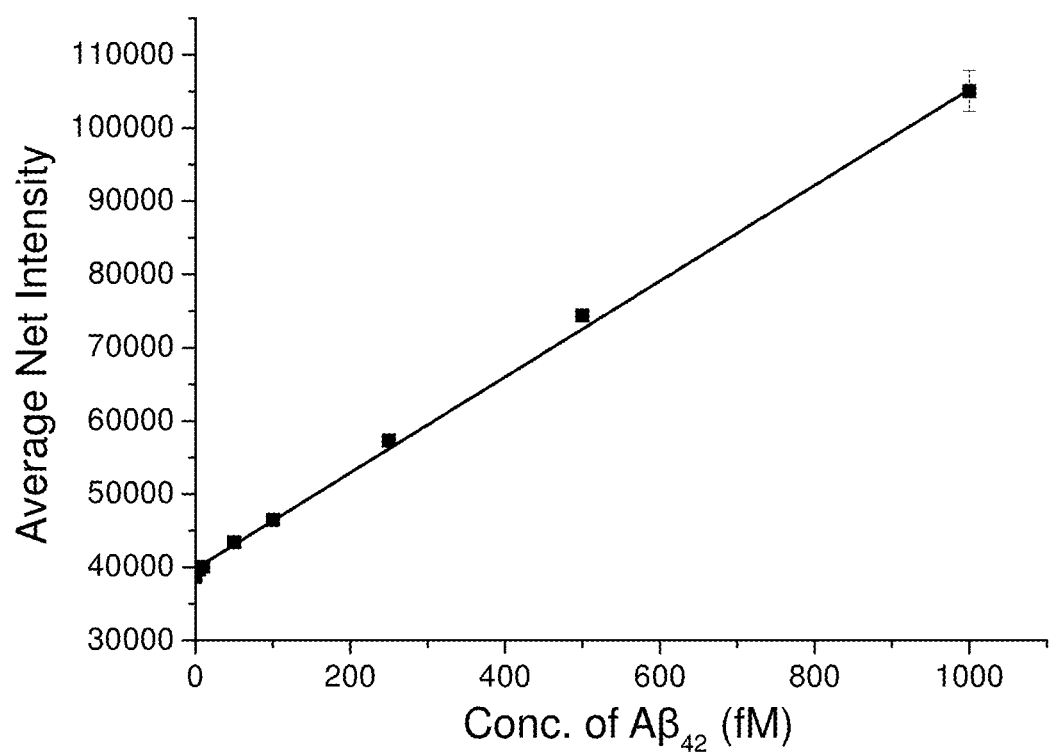
FIG. 7 shows the calibration plot for the quantification of $A\beta_{42}$ using SLAce, different concentrations of $A\beta_{42}$ are incubated with the nanoprobes and the detection antibody. Error bars, standard error of mean n=3. Limit of detection=50 fM.
Figure 8:
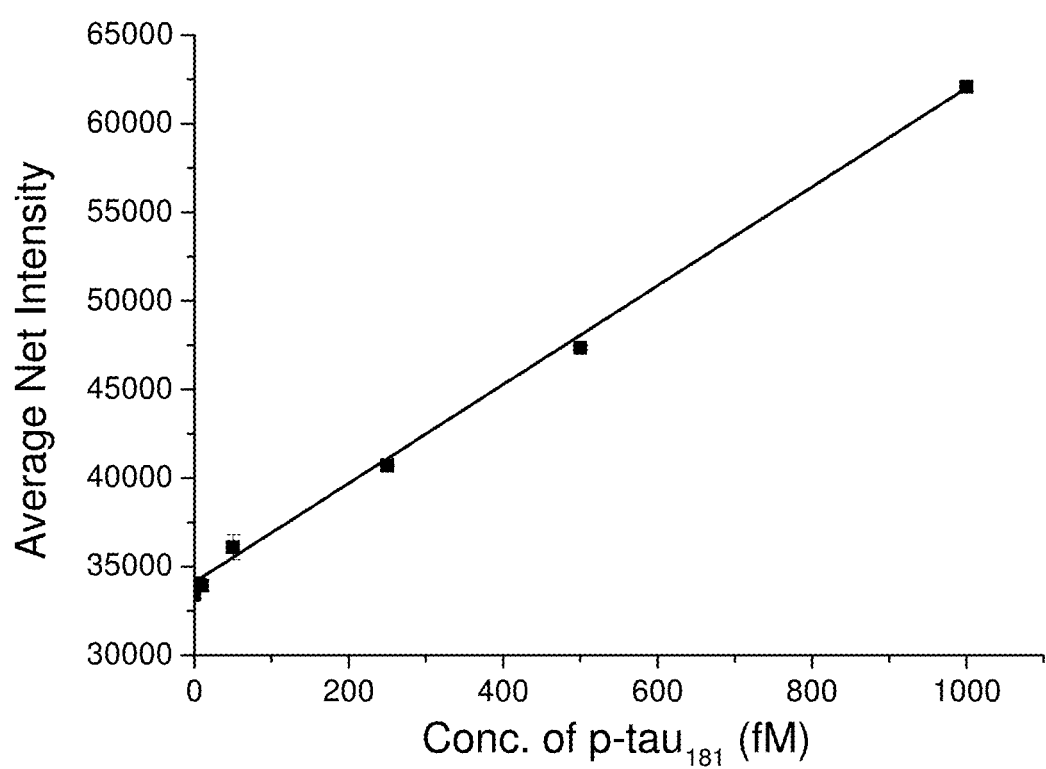
FIG. 8 shows the calibration plot for the quantification of p-$tau_{181}$ using SLAce, different concentrations of p-$tau_{181}$ are incubated with the nanoprobes and the detection antibody. Error bars, standard error of mean n=3. Limit of detection=50 fM.
Figure 9:
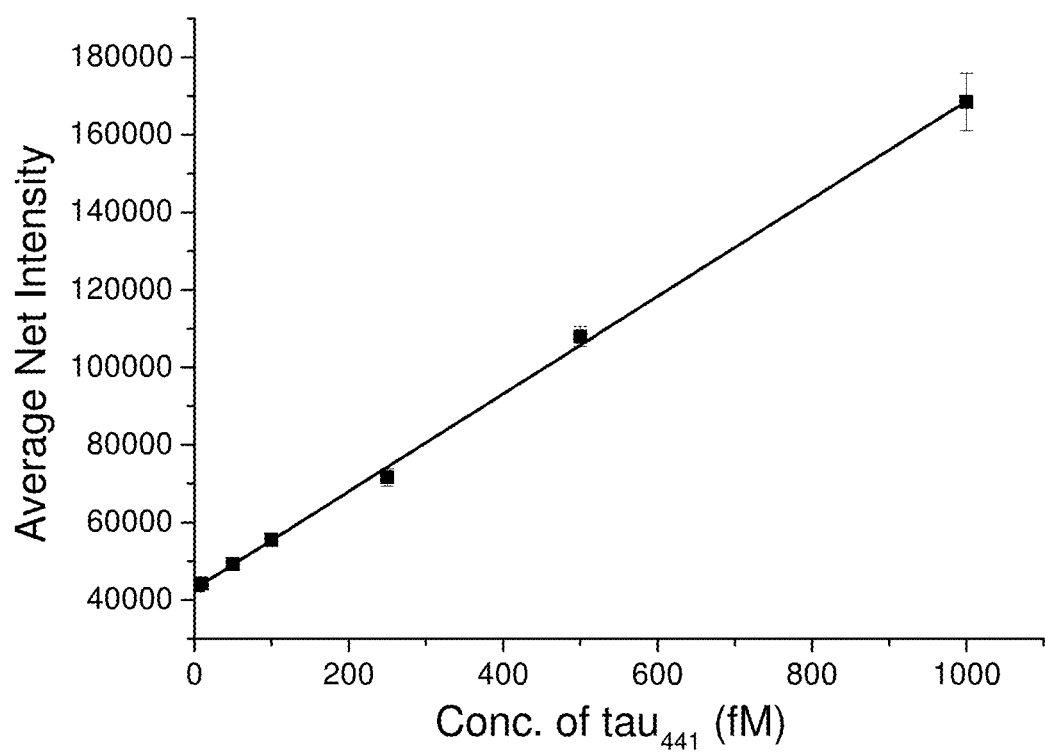
FIG. 9 shows the calibration plot for the quantification of $tau_{441}$ using SLAce, different concentrations of $tau_{441}$ are incubated with the nanoprobes and the detection antibody. Error bars, standard error of mean n=3. Limit of detection=24 fM.

Multiplexity detection refers to the ability of the present invention to detect multiple biomarkers and/or antigens in one sample simultaneously. To demonstrate the multiplexity of the present detection assay, 10 pM of the target antigens, AFP, CEA, and PSA, are incubated with their corresponding Ab1-MNP probes and Ab2 in solution. Then the MICs are further labeled with three fluorophores, namely, SPAce, VLAce, and SLAce. The solution mixture of the MICs is then injected into the flow cell. The fluorescent and first order images are visualized under the TIRFM-EMCCD imaging system coupled with a transmission grating. A 488 nm laser is used as the excitation light source. As shown in FIG. 5, the SPAce labeled AFP MICs, SLAce labeled PSA MICs and VLAce labeled CEA MICs exhibited emission peaks at 570 nm, 650 nm, and 750 nm, respectively. The emission peaks match with the emission peaks of the corresponding fluorophores upon binding to PSA MICs, AFP MICs and CEA MICs. From the first order images and the intensity spectra, MICs can be differentiated from one and other. The quantification of the antigen can be done by simply measuring the fluorescence intensity of the MICs.

Biomarkers for Alzheimer's disease (AD) are used as another example to illustrate the high sensitivity of the present invention for the use in detecting biomarkers in body fluids. 42-amino-acid form of amyloid-β protein ($A\beta_{42}$), total (t-tau) and tau phosphorylated at threonine 181 (p-$tau_{181}$) proteins are found to be important pathological hallmarks for Alzheimer's Disease. Low CSF concentration of Alzheimer's Disease biomarkers especially makes measurement by conventional methods much more challenging. Thus, in order to provide an early and accurate AD diagnosis, the development of an accurate, rapid, sensitive and multiplex detection assay of $A\beta_{42}$, total and phosphorylated tau proteins as the biomarkers is urged.

Figure 10:
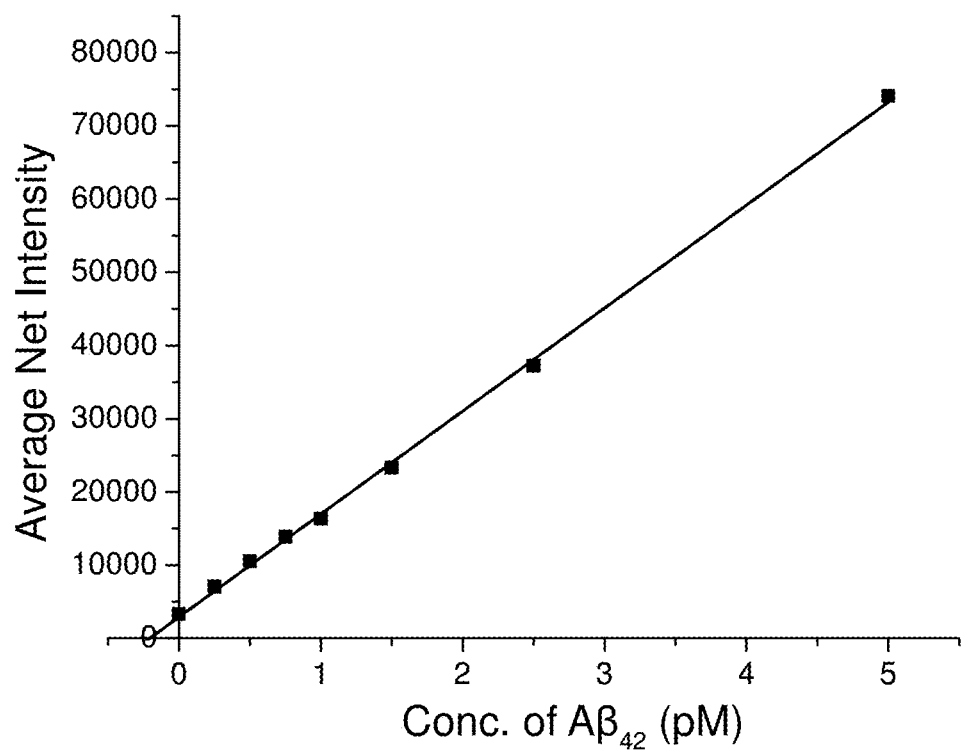
FIG. 10 shows the quantification of $A\beta_{42}$ in human serum sample by standard addition method using SLAce, different concentrations of $A\beta_{42}$ are spiked in and incubated with the nanoprobes, serum sample and the detection antibody. Error bars, standard error of mean n=3.
Figure 11:
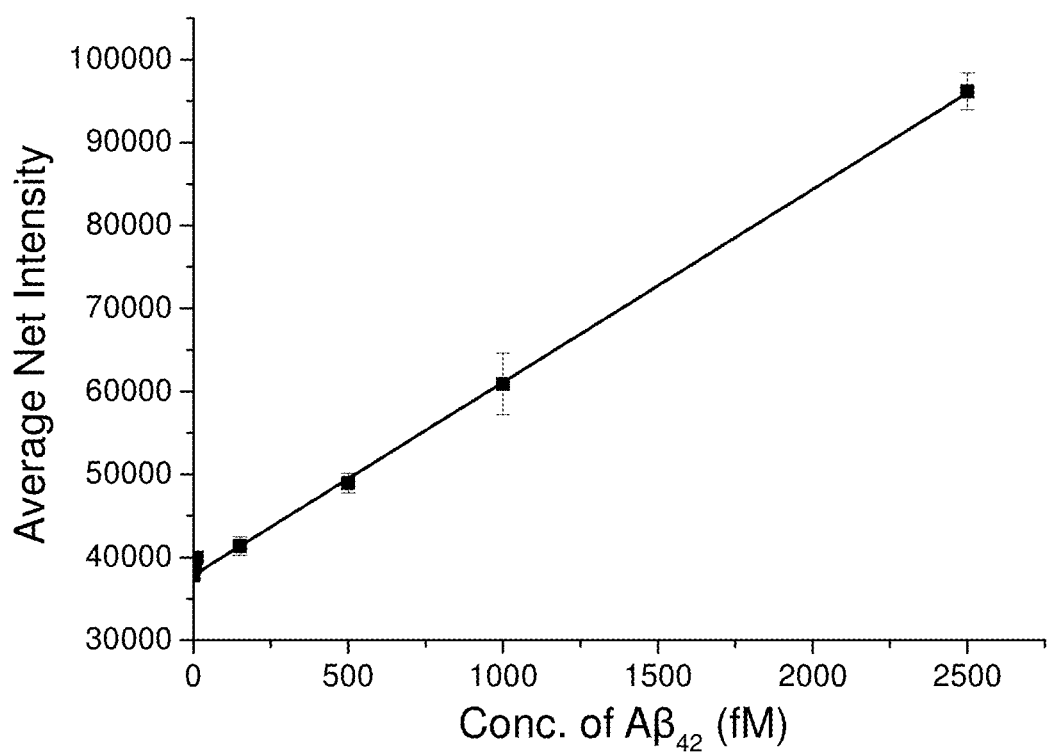
FIG. 11 shows the calibration plot for the quantification of $A\beta_{42}$ using SIM, different concentrations of $A\beta_{42}$ are incubated with the nanoprobes and the detection antibody. Error bars, standard error of mean n=3. Limit of detection=23 fM.
Figure 12:
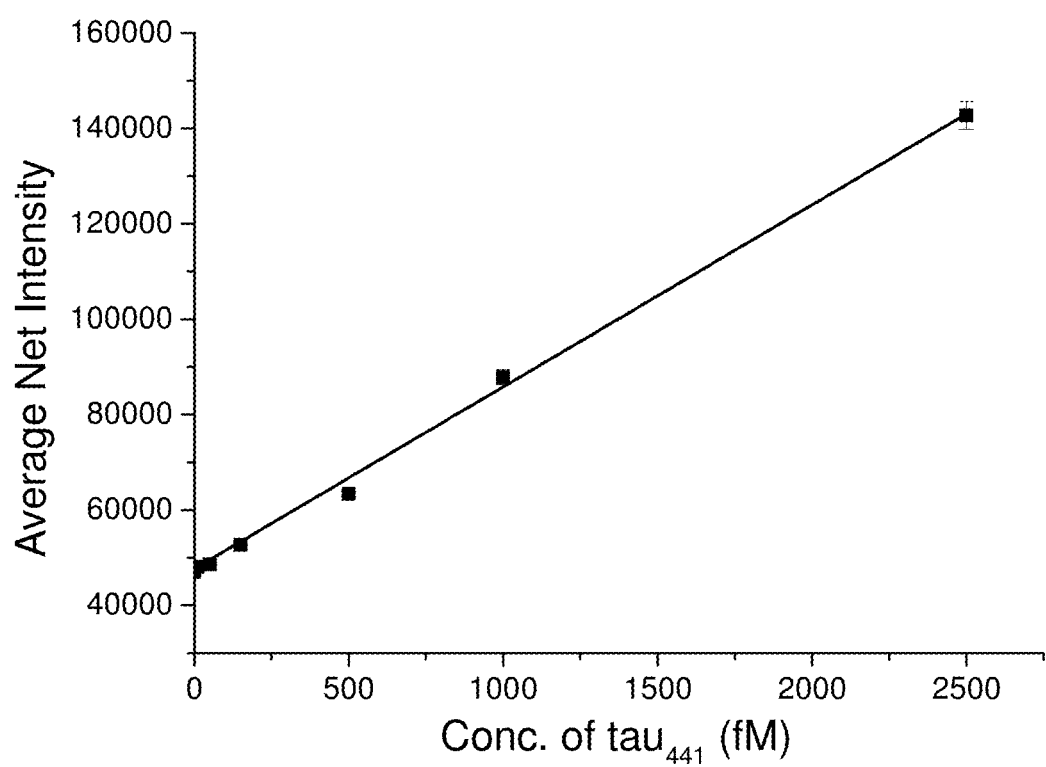
FIG. 12 shows the calibration plot for the quantification of $tau_{441}$ using SIM, different concentrations of $tau_{441}$ are incubated with the nanoprobes and the detection antibody. Error bars, standard error of mean n=3. Limit of detection=14 fM.
Figure 13:
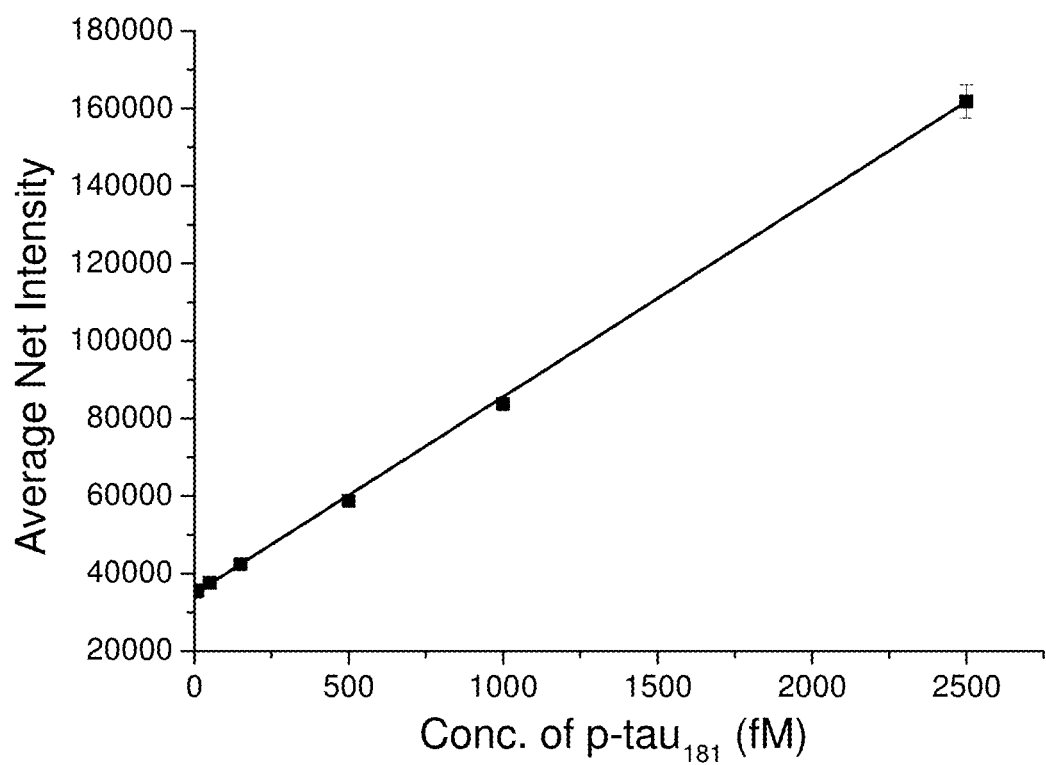
FIG. 13 shows the calibration plot for the quantification of p-$tau_{181}$ using SIM, different concentrations of p-$tau_{181}$ are incubated with the nanoprobes and the detection antibody. Error bars, standard error of mean n=3. Limit of detection=34 fM.
Figure 14:
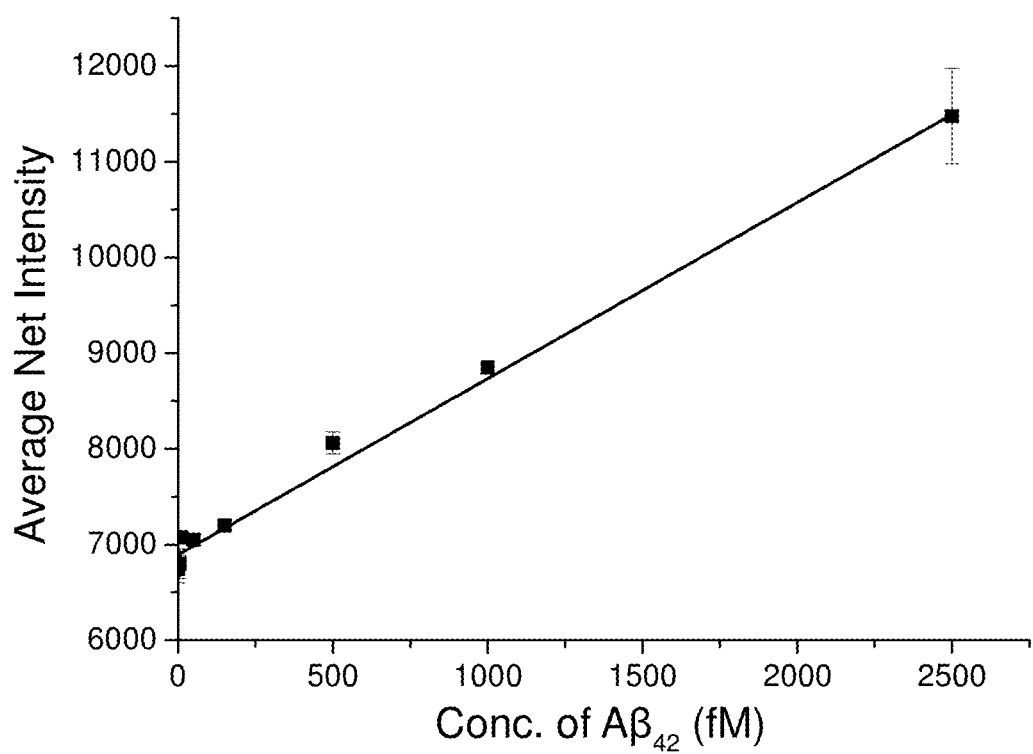
FIG. 14 shows the calibration plot for the quantification of $A\beta_{42}$ using SIOH, different concentrations of $A\beta_{42}$ are incubated with the nanoprobes and the detection antibody. Error bars, standard error of mean n=3. Limit of detection=160 fM.
Figure 15:
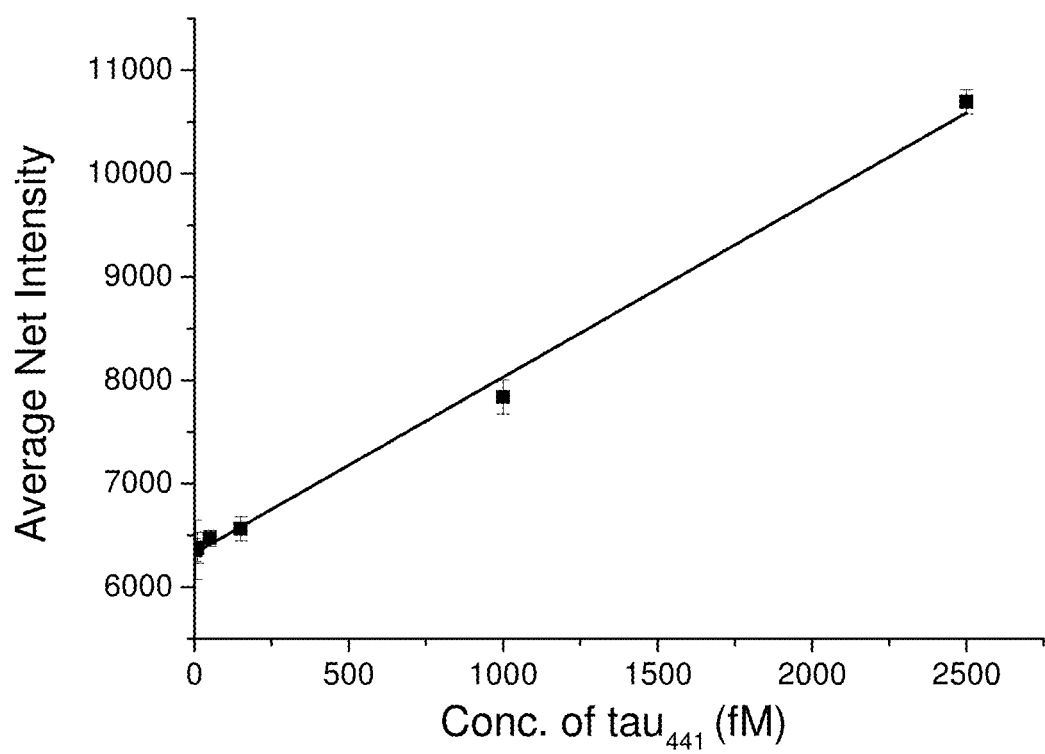
FIG. 15 shows the calibration plot for the quantification of $tau_{441}$ using SIOH, different concentrations of $tau_{441}$ are incubated with the nanoprobes and the detection antibody. Error bars, standard error of mean n=3. Limit of detection=210 fM.
Figure 16:
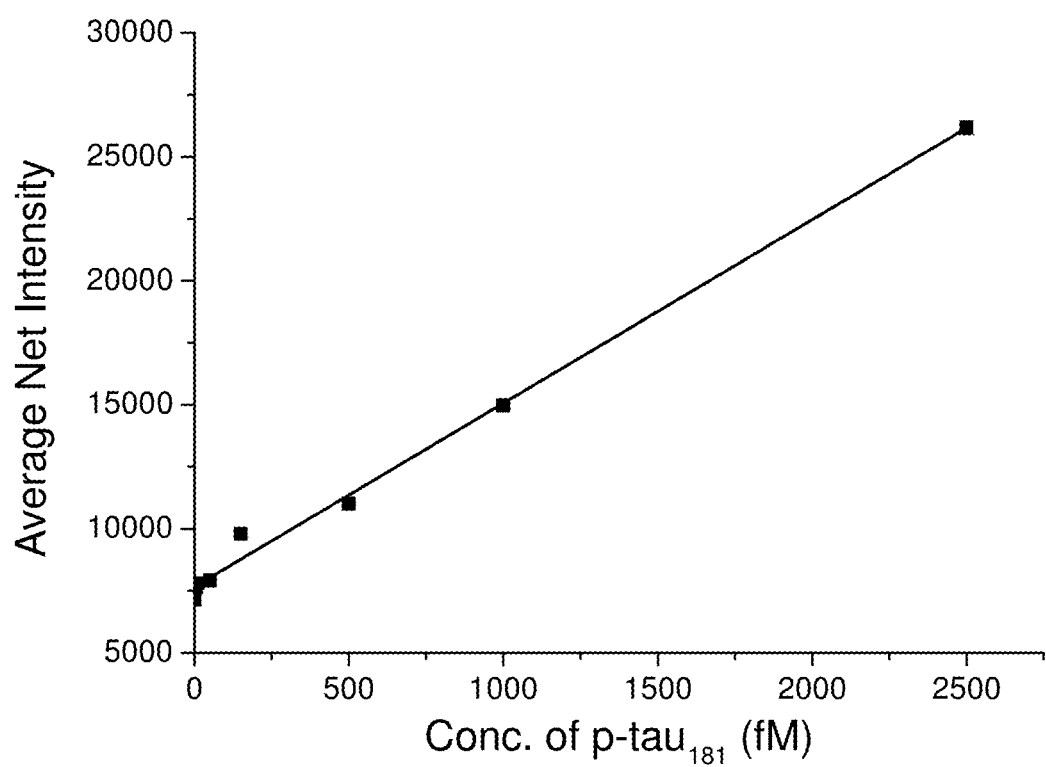
FIG. 16 shows the calibration plot for the quantification of p-$tau_{181}$ using SIOH, different concentrations of p-$tau_{181}$ are incubated with the nanoprobes and the detection antibody. Error bars, standard error of mean n=3. Limit of detection=11 fM.

Herein, the present invention is shown to detect AD protein biomarkers. Calibration plots of the average net intensity as a function of the target peptide/protein concentration are established. $A\beta_{40}$, $A\beta_{42}$, $tau_{441}$, p-$tau_{181}$ of 0-1000 fM are incubated with 300 μg/mL corresponding MICs and 100 pM detection antibodies in 10% artificial CSF (aCSF) matrixes, and labeled with switch-on fluorophore, SLAce. Plots of the average net intensity of 100 MICs as a function of the concentration of $A\beta_{40}$, $A\beta_{42}$, $tau_{441}$, p-$tau_{181}$ in the 10% CSF matrix are obtained with coefficient of determination of 0.9949, 0.9985, 0.9989 and 0.9981. The detection limits of the assay are 50, 50, 24 and 50 fM as illustrated in FIGS. 6-9. The developed assay is capable of determining the $A\beta_{42}$ content in human serum as elucidated from FIG. 10.

Calibration curves for the $A\beta_{42}$, $tau_{441}$, p-$tau_{181}$ are also constructed with two other turn-on fluorophores of the present invention, SIM and SIOH (see structures in FIG. 1), as shown in FIGS. 11-16. Good linearity is observed in femto-to-pico molar regime. The detection limit of SIM and SIOH for these three protein biomarkers are similar to those obtained for SLAce and as summarized in Table 2.

| Switch-on fluorophores | Target antigen | Limit of detection/fm | FIG. |
|---|---|---|---|
| SLAce | $A\beta_{40}$ | 50 | 6 |
| SLAce | $A\beta_{42}$ | 50 | 7 |
| SLAce | p-$tau_{181}$ | 50 | 8 |
| SLAce | $tau_{441}$ | 24 | 9 |
| SIM | $A\beta_{42}$ | 23 | 11 |
| SIM | $tau_{441}$ | 14 | 12 |
| SIM | p-$tau_{181}$ | 34 | 13 |
| SIOH | $A\beta_{42}$ | 160 | 14 |
| SIOH | $tau_{441}$ | 210 | 15 |
| SIOH | p-$tau_{181}$ | 11 | 16 |

Table 2 shows the limit of detection of the present invention
The working examples herein demonstrate the present invention has a limit of detection of 10 fM.

Figure 17:
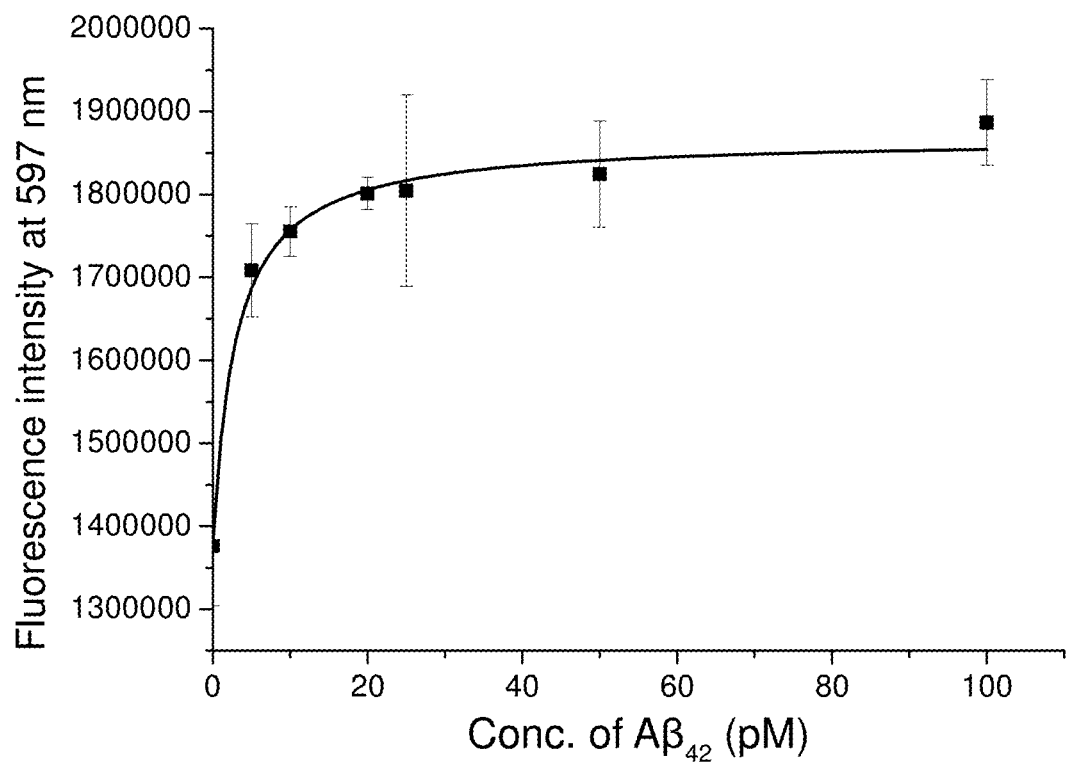
FIG. 17 shows the quantification $A\beta_{42}$ labeled with SIM in the presence of 10% glycerol measured by a spectrofluorimeter.
Figure 18:
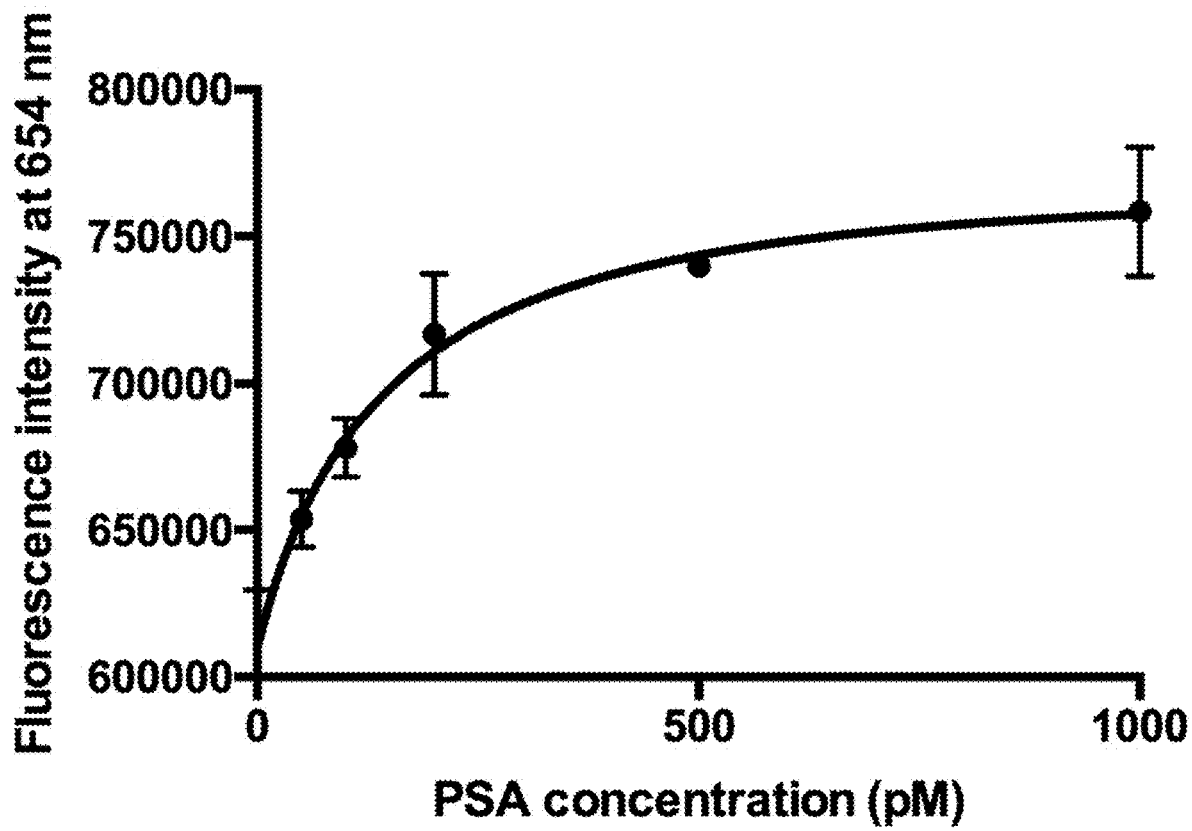
FIG. 18 shows the quantification PSA labeled with SLAce in the presence of 10% glycerol measured by a spectrofluorimeter. A linear range of 0-200 pM of PSA is obtained.

More importantly, the imaging system applicable to the present detection protocol is not limited to TIRFM imaging system. Pico-molar detection limit, concentration of biomarkers in crude body fluids, can be achieved with commercial spectrofluorimeter. Using typical commercial spectrofluorimeter to measure the fluorescence intensity resulting from the target protein biomarkers in accordance with the present invention, detection limit of pico-molar range is shown (FIGS. 17-18).

Figure 19:
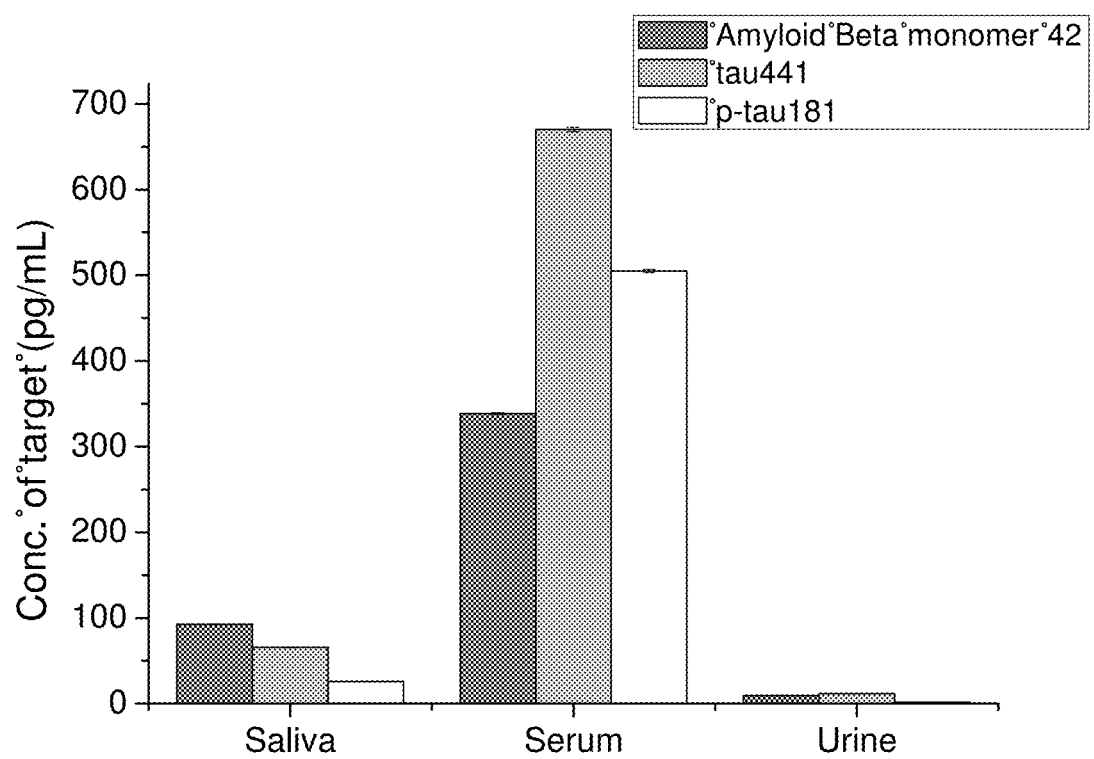
FIG. 19 shows the quantification of the biomarkers in different human biological samples by external calibration.

The capability of the present detection assay in quantification of protein biomarkers in sample of normal donor's and AD patient CSF samples is verified with the ELISA measurement (Table 3). The present invention is also demonstrated to be applicable for the quantification of protein biomarkers in urine and saliva samples as shown in FIG. 19.

TABLE 3

Concentrations of 3 biomarkers in three human CSF sample, young control (7515), elderly control (7577) and AD patient (8014). (% difference = difference between duplicate/sum of duplicate/2 × 100%; Relative standard deviation (RSD), (%) = SD/Mean × 100%; Relative percent difference (RPD), (%) = difference obtained by two methods/concentration obtained by ELISA × 100%)

| Patient # | ELISA (pg/mL) | % Difference | MICs (pg/mL) | RSD (%) | RPD (%) |
|---|---|---|---|---|---|
| $A\beta_{42}$ | | | | | |
| 7515 | 484.05 | 29.97 | 505.09 | 8.26 | 4.4 |
| 7577 | 716.73 | 24.20 | 745.76 | 4.93 | 4.1 |
| 8014 | 178.67 | 14.10 | 203.44 | 1.97 | 13.9 |
| $Tau_{441}$ | | | | | |
| 7515 | 121.52 | 0.17 | 128.04 | 6.64 | 5.4 |
| 7577 | 126.76 | 0.10 | 132.40 | 8.96 | 4.5 |
| 8014 | 708.4 | 1.63 | 811.87 | 3.37 | 14.6 |
| p-$tau_{181}$ | | | | | |
| 7515 | 21.76 | 0.13 | 23.18 | 4.78 | 6.5 |
| 7577 | 23.48 | 0.16 | 24.77 | 1.33 | 5.5 |
| 8014 | 79.25 | 1.10 | 91.59 | 3.72 | 15.6 |

Features and Benefits of One Embodiment of the Present Invention

One embodiment of the present invention is an ultra sensitive and selective immuno-detection method for protein biomarker(s), such as cancer-associated antigens in sera and Alzheimer's disease related proteins, in cerebrospinal fluid.

It is a simple, direct, and purification-free assay for detection of protein biomarkers that uses an antibody bioconjugated magnetic probe and switch-on fluorophores with the aid of total internal reflection fluorescence microscopy TIRFM imaging system. The present method is performed at single nanoparticles level.

The present method is capable of differentiating the target protein molecules from other proteins. It also has the following advantages:

Low detection limit: a limit of detection (LOD) of 200 fM (6.5 pg/mL) and a limit of quantification (LOQ) of 2 pM (0.66 ng/mL) for PSA; LOD of 50 fM for amyloid peptide (1-40), LOD of 50 fM for amyloid peptide (1-42), LOD of 24 fM for tau-protein and LOD of 50 fM for phosphorylated tau-181 proteins in artificial CSF.

Minute sample consumption: only 10 μL of sample;
Fast: the assay can be completed within 1 hour;
Free of sample pretreatment and amplication: no sample loss and contamination, crude sample can be used; and
Multiplex detection is attainable.

The present method serves as an analytical tool for early disease diagnosis, progression monitoring and staging. The present assay can be readily modified as would appreciated by one skilled in the art, such as replacing the antibodies by other diseases or cancer related antibodies, nucleic-acid probes (DNA and/or RNA), aptamers and imaging systems for other biomedical research and disease diagnostics.

Materials and Methods

Synthesis and NMR Characterization of the Switch-On Fluorophores

Scheme 1: Synthesis of SPAce.

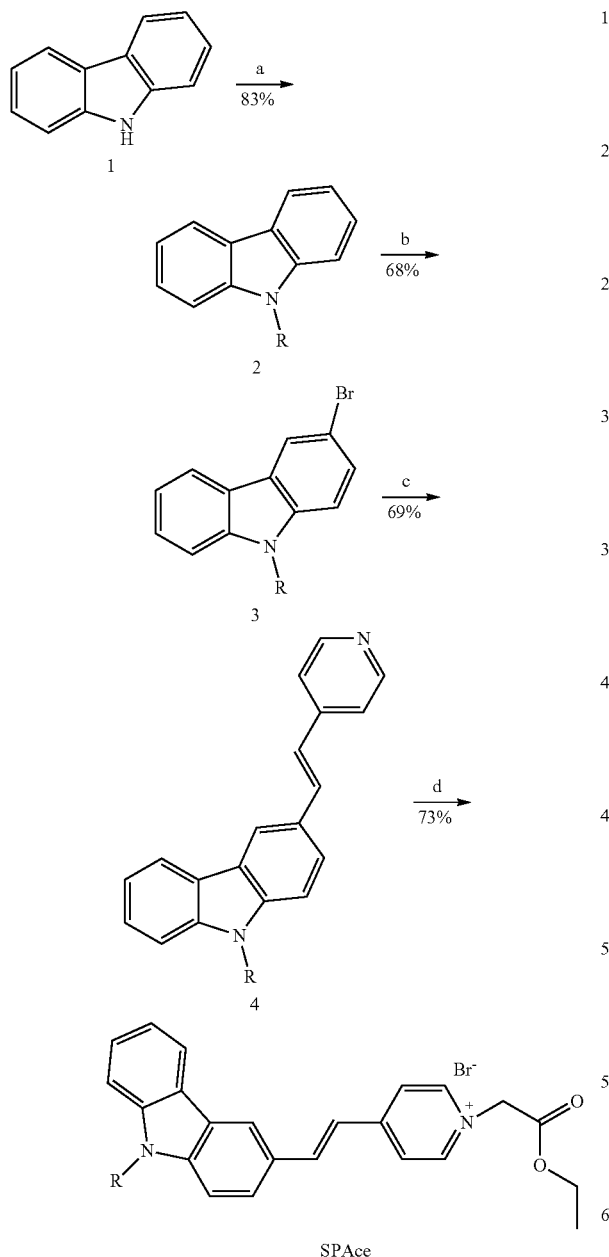

SPAce
R = CH$_3$OCH$_2$CH$_2$OCH$_2$CH$_2$
Reagents and Conditions: a, ClCH$_2$CH$_2$OCH$_2$CH$_2$OCH$_3$, NaH, DMF, 75° C.; b, NBS, DCM, 0° C. to r.t.; c, 4-vinylpyridine, Pd(OAc)$_2$, P(o-tol)$_3$, Et$_3$N, DMF, 90° C.; d, MeCN, BrCH$_2$COOCH$_2$CH$_3$, reflux.

(E)-1-(2-ethoxy-2-oxoethyl)-4-(2-(9-(2-(2-methoxyethoxy)ethyl)-9H-carbazol-3-yl)vinyl)pyridin-1-ium bromide (SPAce) $^1$H NMR (400 MHz, DMSO-d$_6$) δ8.84 (d, J=6.8 Hz, 2H), 8.61 (s, 1H), 8.30-8.26 (m, 3H), 8.20 (d, J=7.6 Hz, 1H), 7.90 (dd, J=1.6 Hz, J=8.8 Hz, 1H), 7.76 (d, J=8.8 Hz, 1H), 7.69 (d, J=8 Hz, 1H), 7.58 (d, J=16.4 Hz, 1H), 7.53-7.49 (m, 1H), 7.31-7.27 (m, 1H), 5.54 (s, 2H), 4.61 (t, J=5.2 Hz, 2H), 4.26 (dd, J=7.2 Hz, J=14.4 Hz, 2H), 3.82 (t, J=5.2 Hz, 2H), 3.47-3.45 (m, 2H), 3.31-3.28 (m, 2H), 3.10 (s, 3H), 1.27 (t, J=7.2 Hz, 3H). $^{13}$C NMR (100 MHz, DMSO-d$_6$) δ166.7, 154.5, 145.2, 143.6, 142.0, 140.9, 126.4, 125.3, 126.2, 122.7, 122.1, 121.3, 120.3, 119.9, 119.8, 110.5, 110.3, 71.2, 69.8, 68.8, 14.0. HRMS (MALDI-TOF) m/z Calcd for C$_{28}$H$_{31}$N$_2$O$_4$ 459.2278 Found 459.2296 [M$^+$]

Scheme 2: Synthesis of SLAce.

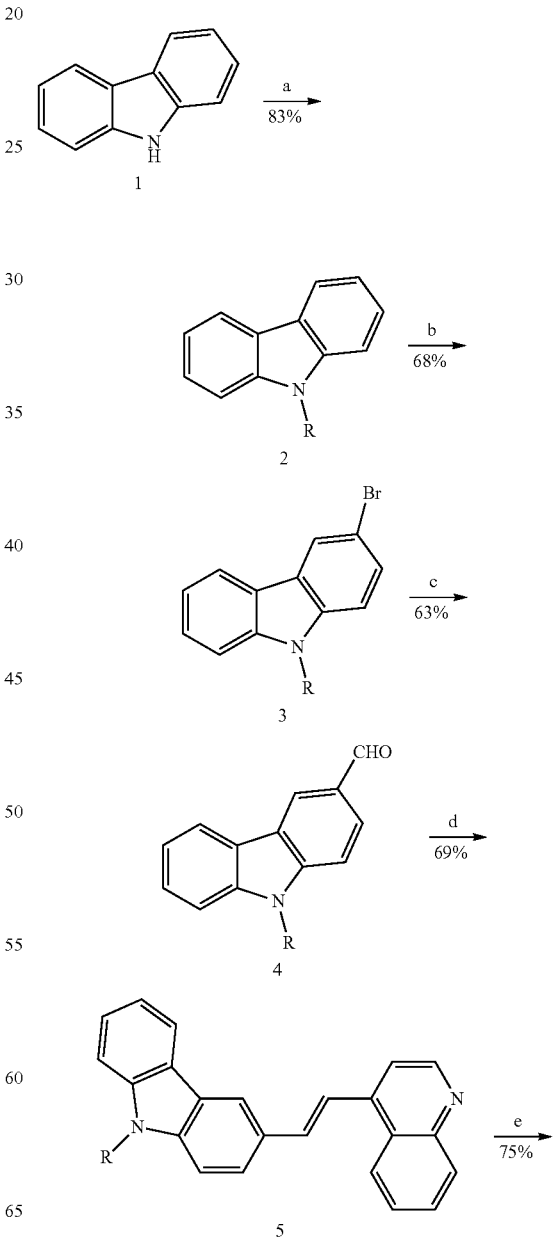

11
-continued

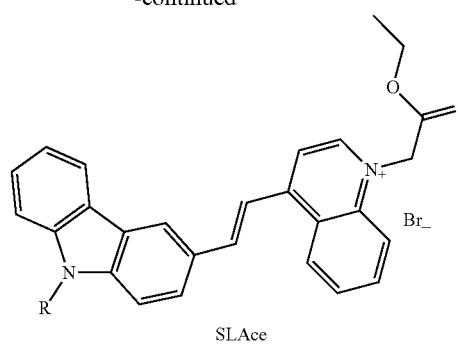

SLAce

R = CH₂OCH₂CH₂OCH₂CH₃
Reagents and Conditions: a, ClCH₂CH₂OCH₂CH₂OCH₃, NaH, DMF, 75° C.; b, NBS, DCM, 0° C. to r.t.; c, n-BuLi, DMF, THF, -78° C.; d, Lepedin, TMSCl, DMF, 100° C., sealed tube; e, MeCN, BrCH₂COOCH₂CH₃, reflux.

Scheme 3: Synthesis of VLAce.

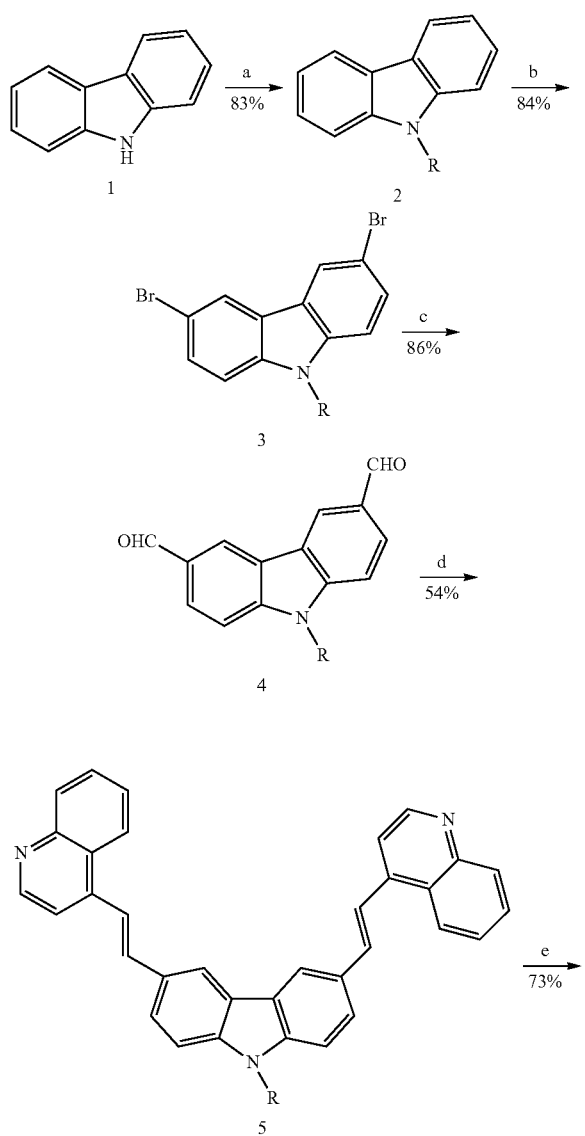

12
-continued

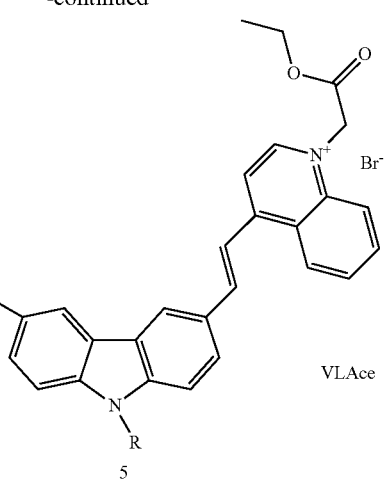

VLAce

R = CH₃OCH₂CH₂OCH₂CH₂
Reagents and Conditions: a, ClCH₂CH₂OCH₂CH₂OCH₃, NaH, DMF, 75° C.; b, NBS, DCM, 0° C. to r.t.; c, n-BuLi, DMF, THF, -78° C.; d, Lepidine, TMSCl, DMF, 100° C., sealed tube; e, MeCN, BrCH₂COOCH₂CH, reflux.

4,4'-(1E,1'E)-(9-(2-(2-methoxyethoxy)ethyl)-9H-carbazole-3,6-diyl)bis(ethene-2,1-diyl))bis(1-(2-ethoxy-2-oxoethyl)quinolin-1-ium) bromide (VLAce). $^1$H NMR (400 MHz, DMSO-d$_6$) δ9.35 (d, J=8.8 Hz, 2H), 9.30 (d, J=6.8Hz, 2H), 9.20 (s, 2H), 8.57 (d, J=6.8 Hz, 2H), 8.44 (s, 4H), 8.27 (d, J=8.8 Hz, 2H), 8.20-8.16 (m, 2H), 8.05 (d, J=8.4 Hz, 2H), 7.99 (t, J=7.6 Hz, 2H), 7.77 (d, J=8.8 Hz, 2H), 6.05 (s, 4H), 4.66 (s, 2H), 4.29-4.24 (m, 4H), 3.89-3.87 (m, 2H), 3.53-3.50 (m, 2H), 3.34-3.32 (m, 2H), 3.11 (s, 3H), 1.27 (t, J=7.2 Hz, 6H). $^{13}$C NMR (100 MHz, DMSO-d$_6$) δ166.5, 154.4, 147.9, 145.9, 142.9, 138.6, 135.3, 129.0, 127.7, 127.2, 126.0, 123.2, 122.3, 118.8, 116.9, 115.2, 110.9, 71.3, 69.8, 68.9, 62.3, 58.1, 56.4, 14.0. HRMS (MALDI-TOF) m/z Calcd for C$_{47}$H$_{47}$N$_3$O$_6$ 750.3537 Found 750.5489[M+1]$^+$.

Scheme 4: Synthesis of SIM.

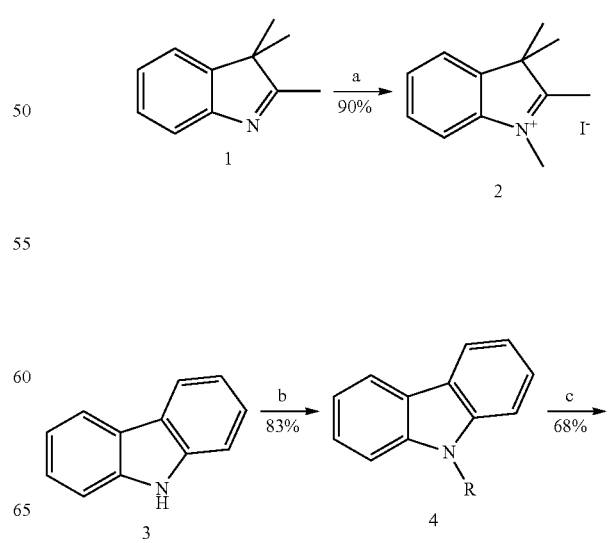

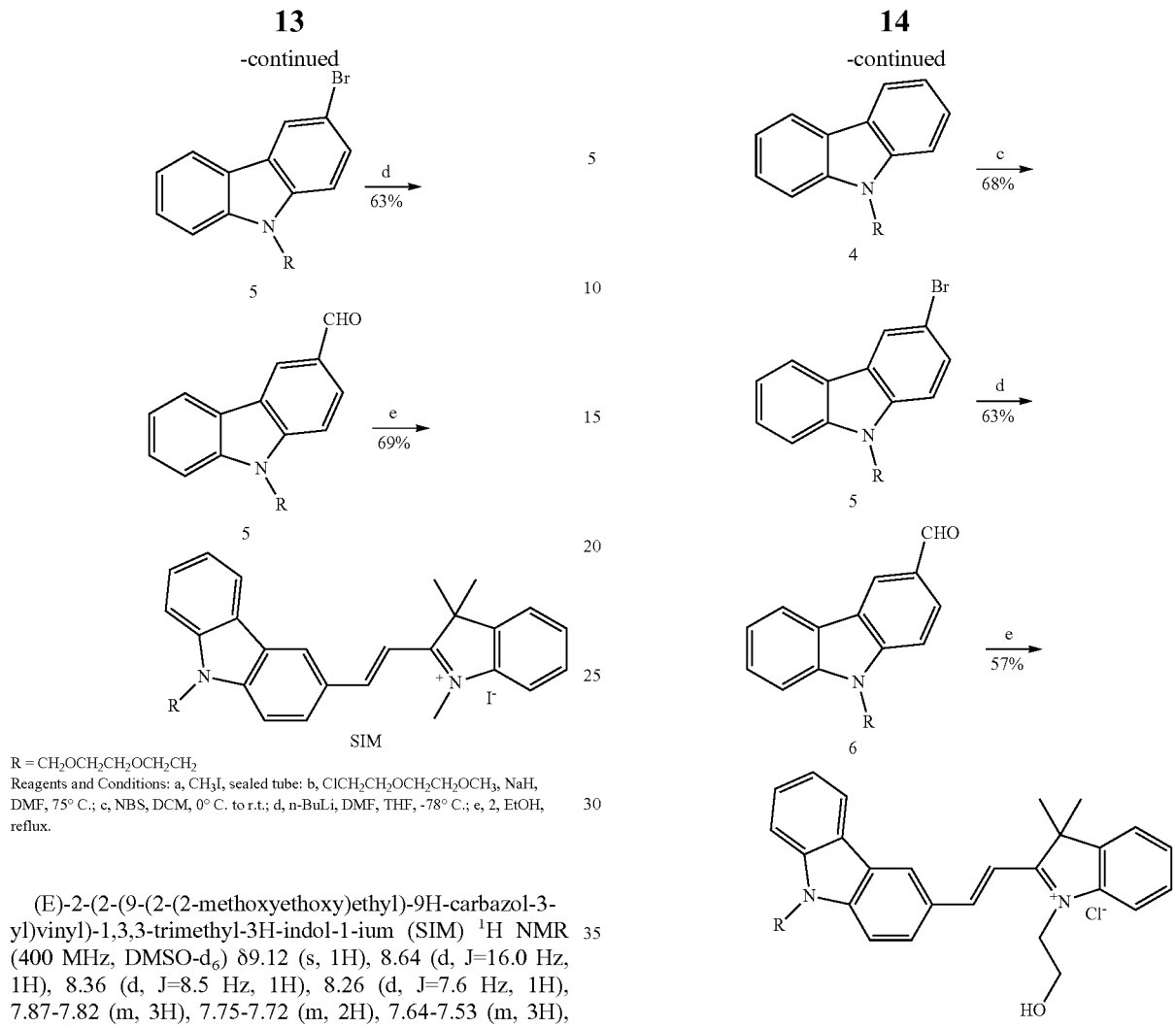

R = CH₂OCH₂CH₂OCH₂CH₂
Reagents and Conditions: a, CH₃I, sealed tube: b, ClCH₂CH₂OCH₂CH₂OCH₃, NaH, DMF, 75° C.; c, NBS, DCM, 0° C. to r.t.; d, n-BuLi, DMF, THF, -78° C.; e, 2, EtOH, reflux.

(E)-2-(2-(9-(2-(2-methoxyethoxy)ethyl)-9H-carbazol-3-yl)vinyl)-1,3,3-trimethyl-3H-indol-1-ium (SIM) $^1$H NMR (400 MHz, DMSO-d$_6$) δ9.12 (s, 1H), 8.64 (d, J=16.0 Hz, 1H), 8.36 (d, J=8.5 Hz, 1H), 8.26 (d, J=7.6 Hz, 1H), 7.87-7.82 (m, 3H), 7.75-7.72 (m, 2H), 7.64-7.53 (m, 3H), 7.38-7.34 (m, 1H), 4.68-4.65 (m, 2H), 4.16 (s, 3H), 3.85-3.83 (m, 2H), 3.48-3.45 (m, 2H), 3.30-3.27 (m, 2H), 3.09 (s, 3H), 1.85 (s, 6H).$^{13}$C NMR (100 MHz, DMSO-d$_6$) δ181.1, 155.1, 143.9, 143.2, 141.9, 141.1, 128.9, 128.6, 126.8, 125.8, 124.8, 123.1, 122.8, 122.3, 120.6, 114.5, 110.9, 110.8, 109.3, 71.3, 69.8, 68.8, 58.1, 51.7, 43.1, 34.1, 25.8. HRMS (MALDI-TOF) m/z Calcd for C$_{30}$H$_{33}$N$_2$O$_2$ 453.2537 Found 453.2544[M⁻]

Scheme 5 Synthesis of SIOH.

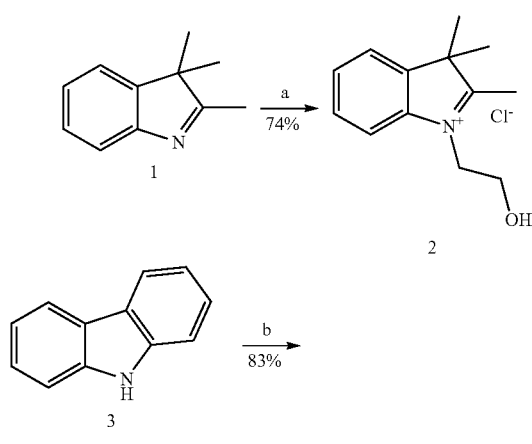

R = CH₂OCH₂CH₂OCH₂CH₂
Reagents and Conditions: a, ClCH₂CH₂OH, sealed tube; b, ClCH₂CH₂OCH₂CH₂OCH₃, NaH, DMF, 75° C.; c, NBS, DCM, 0° C. to r.t.; d, n-BuLi, DMF, THF, -78° C.; e, 2, EtOH, reflux.

1-(2-hydroxyethyl)-2,3,3-trimethyl-3H-indol-1-ium (2) $^1$H NMR (400 MHz, DMSO-d$_6$) δ8.01-7.98 (m, 1H), 7.85-7.83 (m, 1H), 7.62-7.59 (m, 2H), 4.62-4.60 (m, 2H), 3.87-3.85 (m, 2H), 2.85 (s, 3H), 1.55 (s, 6H). $^{13}$C NMR (100 MHz, DMSO-d$_6$) δ197.7, 141.8, 141.2, 129.3, 128.8, 123.4, 115.7, 57.7, 54.3, 50.4, 22.1, 14.5. HRMS (MALDI-TOF) m/z Calcd for C$_{32}$H$_{33}$N$_2$O$_4$ 509.2446 Found 509.2427[M⁺]

(E)-1-(2-hydroxyethyl)-2-(2-(9-(2-(2-methoxyethoxy)ethyl)-9H-carbazol-3-yl)vinyl)-3,3-dimethyl-3H-indol-1-ium (SIOH)$^1$H NMR (400 MHz, DMSO-d$_6$) 69.13 (s, 1H), 8.65 (d, J=16.0 Hz, 1H), 8.35-8.33 (m, 1H), 8.28 (d, J=8.0 Hz, 1H), 7.88-7.86 (m, 2H), 7.83-7.79 (m, 2H), 7.74 (d, J=8.0 Hz, 1H), 7.62-7.53 (m, 3H), 7.37-7.34 (m, 1H), 4.84-4.81 (m, 2H), 4.67-4.65 (m, 2H), 3.94 (d, J=4.0 Hz, 2H), 3.84 (t, J=4.0 Hz, 2H), 3.47-3.45 (m, 2H), 3.29-3.27 (m, 2H), 3.08 (s, 3H), 1.86 (s, 6H). $^{13}$C NMR (100 MHz, DMSO-d$_6$) 6182.5, 155.2, 143.9, 143.4, 141.2, 128.8, 128.7, 128.6, 126.9, 125.9, 124.9, 123.1, 122.9, 122.3, 120.7, 120.6, 115.0, 110.9, 110.8, 109.9, 71.3, 69.8, 68.8, 58.7, 58.1, 51.9, 48.9, 43.1, 26.3. HRMS (MALDI-TOF) m/z Calcd for C$_{31}$H$_{35}$N$_2$O$_3$ 483.2642 Found 483.2649[M⁺]

Coverslide Pretreatment and Preparation of Flow Cell

All coverslides are prewashed prior to use. Sealed flow cell is prepared by combining the prewashed coverslides with double-sided adhesive tape. Each channel is approximated 3 mm wide.

Synthesis of the Silica Coated Iron Oxide Nanoparticles

Aqueous dispersions of magnetic iron oxide nanoparticles are prepared according to Massart's method. Briefly, 4 mL of 1 M iron (III) chloride hexahydrate (Sigma Aldrich, USA) and 1 mL of 2 M iron (II) chloride tetrahydrate (Sigma Aldrich, USA) in 2 M HCl are added to 50 mL of 0.7 M $NH_4OH$ under rapid mechanical stirring. The silica coating is prepared generally by adding iron oxide nanoparticles to a mixture of ammonium hydroxide, $H_2O$, and ethanol, then an ethanolic solution of TEOS (Aldrich, USA) (2 mL TEOS in 30 mL ethanol) is added to the mixture under stirring. The resultant nanoparticles are washed with filtered water thrice in each step and separated by a magnetic field. The transmission electron microscopy (TEM) imaging of the nanoparticles is done by applying 5 µL of the diluted nanoparticles onto a carbon-coated copper grid (T200H-Cu, Electron Microscopy Science, USA) and dried at ambient condition.

Preparation of the Nanoparticles/Capturing Antibody Nanocomposite

Amino-functionalized particles are prepared by using APTES as silylation agent. Conjugation of the capture antibody is done by using the cross-linking reagent, glutaraldehyde (GA).

Quantification of Protein Biomarkers with the Nanocomposite

The detection is based on the formation of sandwiched immunocomplex among the nanoparticles probe, the target biomarker and detection antibody (Ab2). The resultant immunocomplex is further labeled with the fluorophores. The calibration curve of the assay is constructed by correlating the average net intensity of 50-100 individual nanoparticles at each concentration of spiked protein biomarkers. The resultant nanocomposite is labeled with the fluorophores.

Selectivity of the Assay

To study the selectivity of the assay, other protein biomarkers having a final concentration of 50 pM are incubated with optimal amount of detection antibody at 37° C. for 1 hour. The fluorescence intensity of 50-100 individual nanoparticles is measured.

Imaging System and Data Analysis

The prism-type total internal reflection fluorescence is setup. Generally, the flow cell is placed between a fused-silica isosceles prism (CVI, laser USA) and a 60× oil-type objective that equipped on an Olympus IX71 inverted microscope with a BLP-488R long pass filter (Semrock, USA). A 488 nm diode laser (Newport, USA) is used as the excitation source to excite the fluorophore. An Electron Multiplying Charge Coupled Device (EMCCD) (Photon-Max 512, Princeton Instrument, USA) incorporated with a Uniphase mechanical shutter (Model LS2Z2, Vincent Associates, USA) and a driver (Model VMM-T1, Vincent Associates, USA) in external synchronization and frame-transfer mode are used. All the images are analyzed by a public-domain image processing software Image J.

INDUSTRIAL APPLICABILITY

The present invention discloses a magnetic platform for direct and multiplex immune-based detection of trace amount of protein biomarkers for cancers, neurodegenerative disease such as Alzheimer's disease If desired, the different functions discussed herein may be performed in a different order and/or concurrently with each other. Furthermore, if desired, one or more of the above-described functions may be optional or may be combined.

While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extent. All publications recited herein are hereby incorporated by reference in their entirety.

The invention claimed is:

1. A method for detecting a target biomarker in a sample comprising a biological medium comprising:
   providing at least one detection probe, wherein the at least one detection probe comprises at least one capturing antibody conjugated onto the surface of a silicon-coated magnetic nanoparticle;
   contacting said at least one detection probe and at least one detection antibody into said sample to capture at least one target antigen, wherein said target antigen is said target biomarker or is an antigen associated with said target biomarker, thereby forming at least one magnetic immuno-composite;
   contacting said magnetic immuno-composite with a plurality of unconjugated switched-on fluorophores to form at least one fluorescent magnetic immuno-composite, wherein the plurality of unconjugated switched-on fluorophores bind to said at least one magnetic immune-composite via in least one interaction selected from the group consisting of electrostatic interactions and hydrophobic interactions and the plurality of unconjugated switched-on fluorophores have the structure:

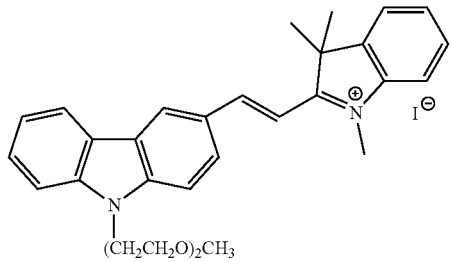

separating said at least one fluorescent magnetic immuno-composite from the biological medium using an external magnetic field thereby forming a separated fluorescent magnetic immune-composite, and
detecting said separated fluorescent magnetic immuno-composite using at least one fluorescent detection means.

2. The method according to claim 1 wherein said target biomarker comprise protein biomarkers.

3. The method according to claim 1 wherein said biological medium comprises bodily fluids selected from the group consisting of sera, urine, saliva and cerebrospinal fluid.

4. The method according to claim 1 wherein said at least one silicon-coated magnetic nanoparticle comprises silicon-coated iron oxide nanoparticles.

5. The method according to claim 1 wherein said at least one target antigen comprises prostate specific antigen, carcinoembryonic antigen, alpha-fetoprotein, Alzheimer's Diseases protein biomarkers, or a combination thereof.

6. The method according to claim 1 wherein said external magnetic field is created by one or more external magnets.

7. The method according to claim 1 wherein said at least one fluorescent detection means comprises fluorescent microscopy, fluorescence spectroscopy, or a combination thereof.

\* \* \* \* \*